United States Patent [19]

Uyama et al.

[11] Patent Number: 4,907,157
[45] Date of Patent: Mar. 6, 1990

[54] METHOD AND SYSTEM FOR ALLOWING IMAGING OF ANY SIZE OBJECT THROUGH USE OF SEPARATE SOURCE AND DETECTOR UNIT

[75] Inventors: Kiichiro Uyama; Shigeo Nakamura, both of Tokyo, Japan

[73] Assignee: Kabushiki Kaisha Toshiba, Kawasaki, Japan

[21] Appl. No.: 770,248

[22] Filed: Aug. 28, 1985

[30] Foreign Application Priority Data

Sep. 5, 1984 [JP] Japan ............................ 59-185711
Sep. 5, 1984 [JP] Japan ............................ 59-185712
Dec. 28, 1984 [JP] Japan ............................ 59-276246

[51] Int. Cl.$^4$ ............................................ G06F 15/42
[52] U.S. Cl. ........................ 364/413.13; 378/20; 378/11; 378/196; 364/413.15
[58] Field of Search ............ 378/26, 196, 11, 13, 378/20, 901; 364/414, 413.13–413.15

[56] References Cited

U.S. PATENT DOCUMENTS

| | | | |
|---|---|---|---|
| 4,082,955 | 4/1978 | Sell | 378/196 |
| 4,264,820 | 4/1981 | Hotta | 250/439 P |
| 4,283,629 | 8/1981 | Habermehl | 378/4 |
| 4,284,896 | 8/1981 | Stonestrome | 364/414 |
| 4,315,156 | 2/1982 | Sell | 378/196 |
| 4,384,209 | 5/1983 | Wagner | 364/414 |
| 4,422,177 | 12/1983 | Mastronardi | 378/10 |
| 4,578,753 | 3/1986 | Crawford | 364/414 |
| 4,639,941 | 1/1987 | Hounsfield | 364/414 |

FOREIGN PATENT DOCUMENTS 2846702 5/1987 Fed. Rep. of Germany .
2019688 10/1979 United Kingdom .

Primary Examiner—Jerry Smith
Assistant Examiner—Gail O. Hayes
Attorney, Agent, or Firm—Oblon, Spivak, McClelland, Maier & Neustadt

[57] ABSTRACT

A tomographic apparatus includes a movable radiation generating system and a movable radiation sensing system which may be placed independently of the location of the radiation generating system. The locus of movement of a radiation generating point is adjusted to be parallel to the arrangement of the radiation sensing system. The distance between the generating and sensing systems is obtained by a prescribed calculation. The CT scanning starts after initializing the radiation generating/sensing systems. Then, projecting data of the inspection object is obtained. Thereafter, image reconstruction processing is performed onto the obtained projection data in accordance with a sequential approximation method, so that a tomographic image of the object is produced. According to the above tomographic apparatus, since the movable radiation sensing system is independent of and optionally separated from the movable radiation generating system, it is possible to obtain the tomographic image of a large object, even if such an object cannot be moved and/or any obstructions exist around the object.

17 Claims, 25 Drawing Sheets

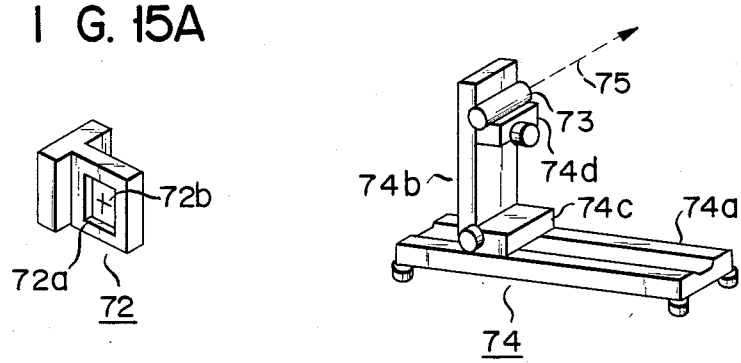
FIG. 15A
FIG. 15B
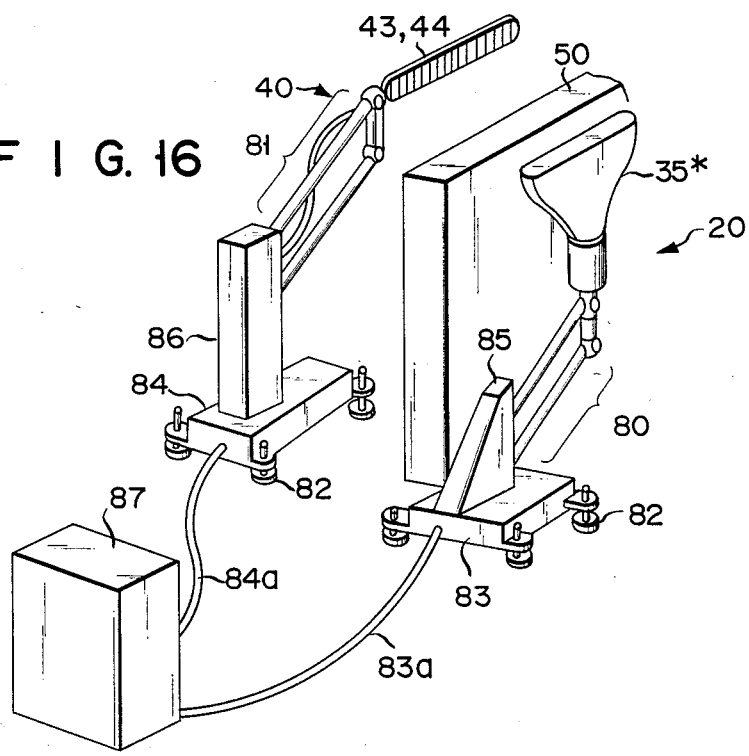
FIG. 16

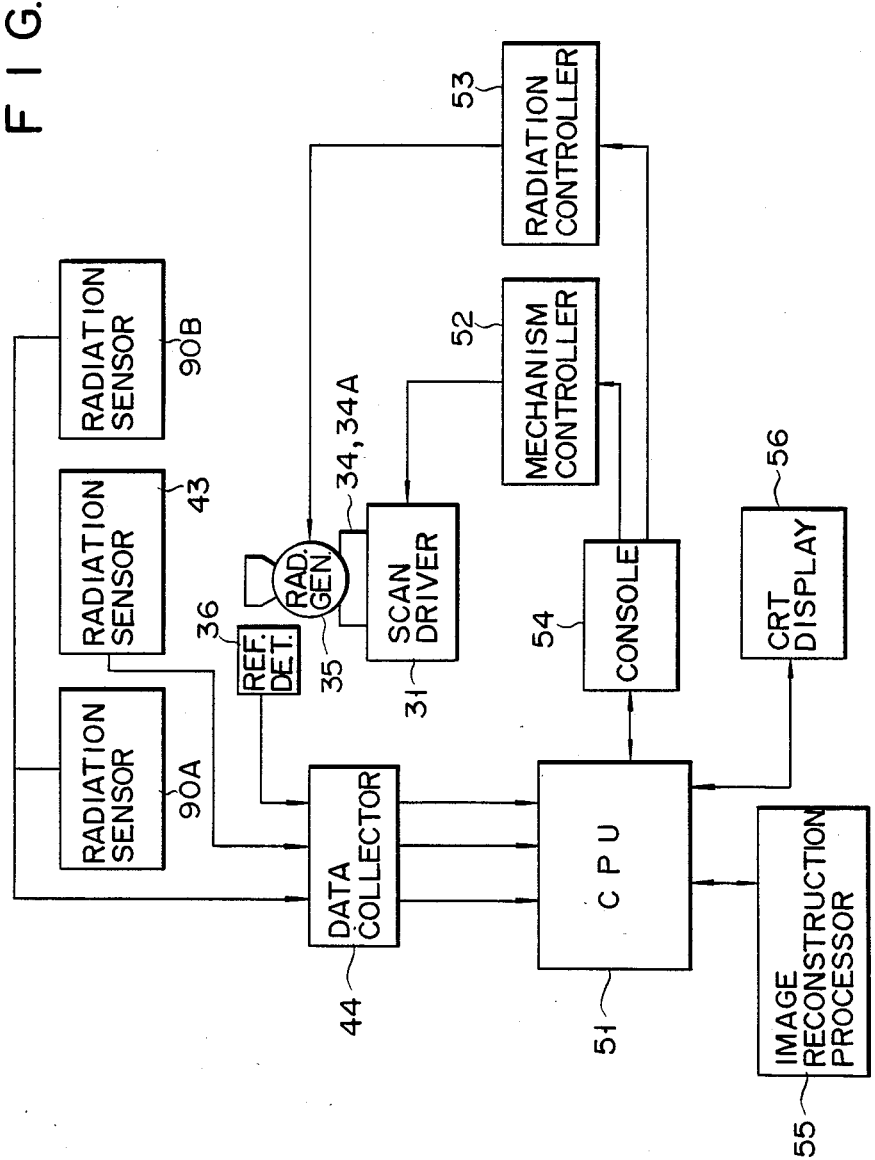

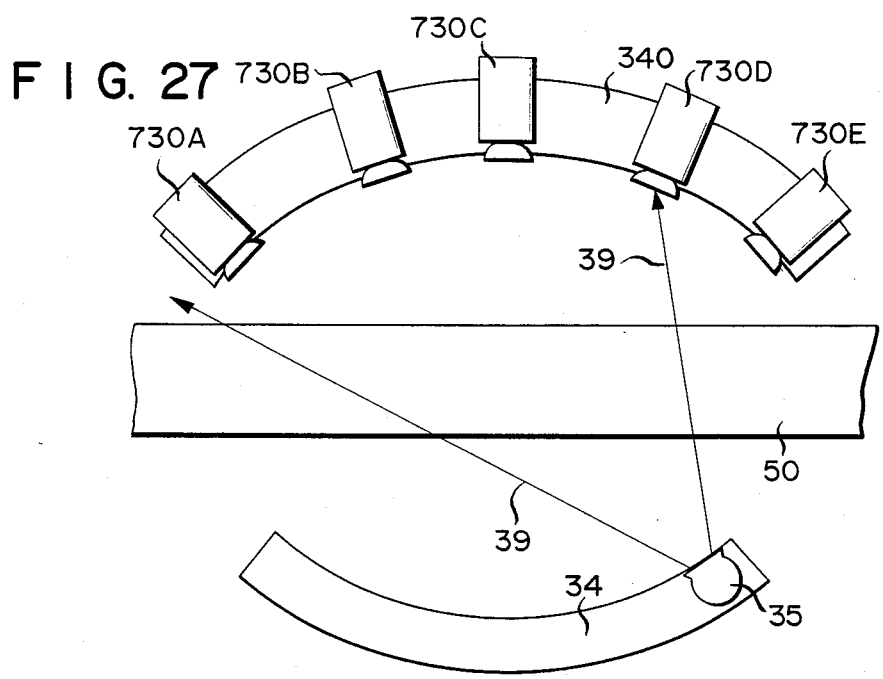
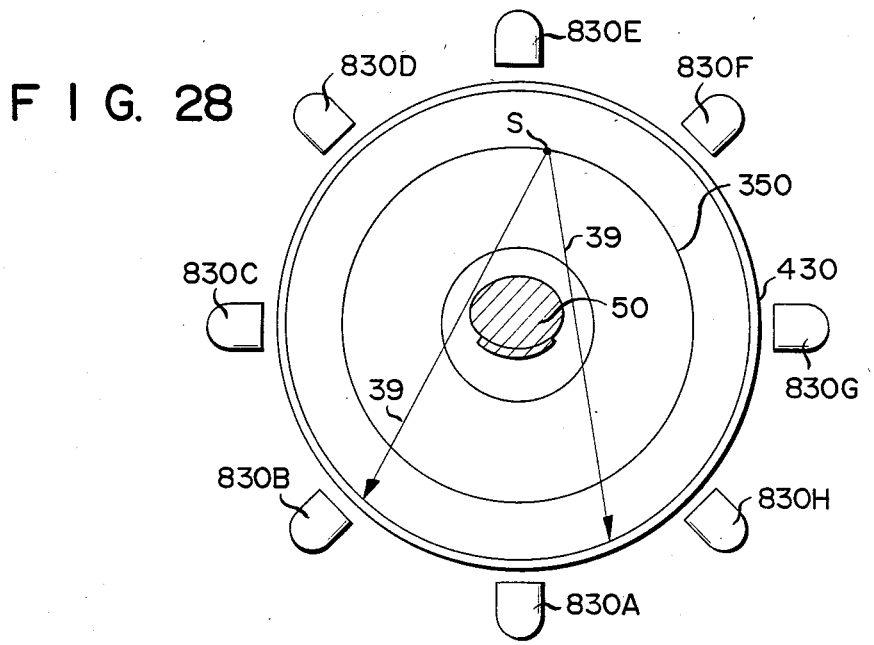

METHOD AND SYSTEM FOR ALLOWING IMAGING OF ANY SIZE OBJECT THROUGH USE OF SEPARATE SOURCE AND DETECTOR UNIT

BACKGROUND OF THE INVENTION

The present invention relates to a tomographic apparatus suitable for nondestructively inspecting industrial manufactures or the materials thereof, and particularly to a CT apparatus provided with independent movable radiation generating/sensing systems.

CT apparatuses are conventionally used for material purposes to obtain a tomographic image (CT image) of a human body, or for industrial purposes to nondestructively test various objects. Such a CT apparatus is known from U.S. Pat. No. 4,075,492 (Boyd et al.), U.S. Pat. No. 4,138,721 (Boyd), U.S. Pat. No. 4,149,247 (Pavkovich et al.), U.S. Pat. No. 4,280,178 (Nassi et al.), U.S. Pat. No. 4,293,912 (Walters), etc. (All disclosures of these U.S. Patents are incorporated by reference in the present application.)

In general, a scanner main body of the above CT apparatus is settled or fixed in a specific scanner room. In this case, the object to be inspected must be carried into the scanner room. This restricts the kind, size and/or weight of the object that can be inspected. In addition, according to a known algorithm for reconstructing a CT image, an X ray generator/sensor pair of the CT apparatus has to be rotated around the object to be inspected by an angle of at least the sum of 180 degrees and the X ray fan beam angle. Therefore, even if the object (e.g., a construction body) to be inspected can be carried into the scanner room, it is often impossible to obtain a complete reconstructed CT image of the object, because the rotation of the generator/sensor pair over 180 degrees is impossible.

SUMMARY OF THE INVENTION

It is accordingly an object of the present invention to provide a tomographic apparatus which is not hindered by practical restrictions such as the kind, size, weight, etc. of the object to be inspected.

To achieve the above object a tomographic apparatus of the invention includes a movable radiation generating system and a movable radiation sensing system which may be located independently of the radiation generating system. The locus of movement of a radiation generating point is adjusted, e.g., to be parallel to the arrangement of the radiation sensing system. The distance between the generating and sensing systems is obtained by a prescribed calculation. The CT scanning starts after initializing the radiation generating/sensing systems, and projection data of the object is obtained. Thereafter, image reconstruction processing is performed on the obtained projection data in accordance with a sequential approximation method, so that a CT image of the object is produced.

According to the above tomographic apparatus, since the movable radiation sensing system is independent of and separated from the movable radiation generating system, it is possible to obtain a CT image of a large object, even if such an object cannot be moved and/or an obstruction exists near it.

BRIEF DESCRIPTION OF THE DRAWINGS

FIG. 15A is a perspective view of a positioning indicator (72) used in the embodiment of FIG. 14;

FIG. 15B is a perspective view of a laser light device (74) adapted to the embodiment of FIG. 14;

FIG. 16 shows still another embodiment of a tomographic apparatus according to the present invention;

FIG. 18 shows a block configuration of the electrical part of the embodiment of FIG. 17;

FIG. 27 shows a tomographic apparatus according to another embodiment of the invention;

FIG. 28 shows a tomographic apparatus according to another embodiment of the invention;

DETAILED DESCRIPTION OF THE PREFERRED EMBODIMENTS

In the following, the preferred embodiments of the present invention will be described in detail with reference to the accompanying drawings.

Figure 1:
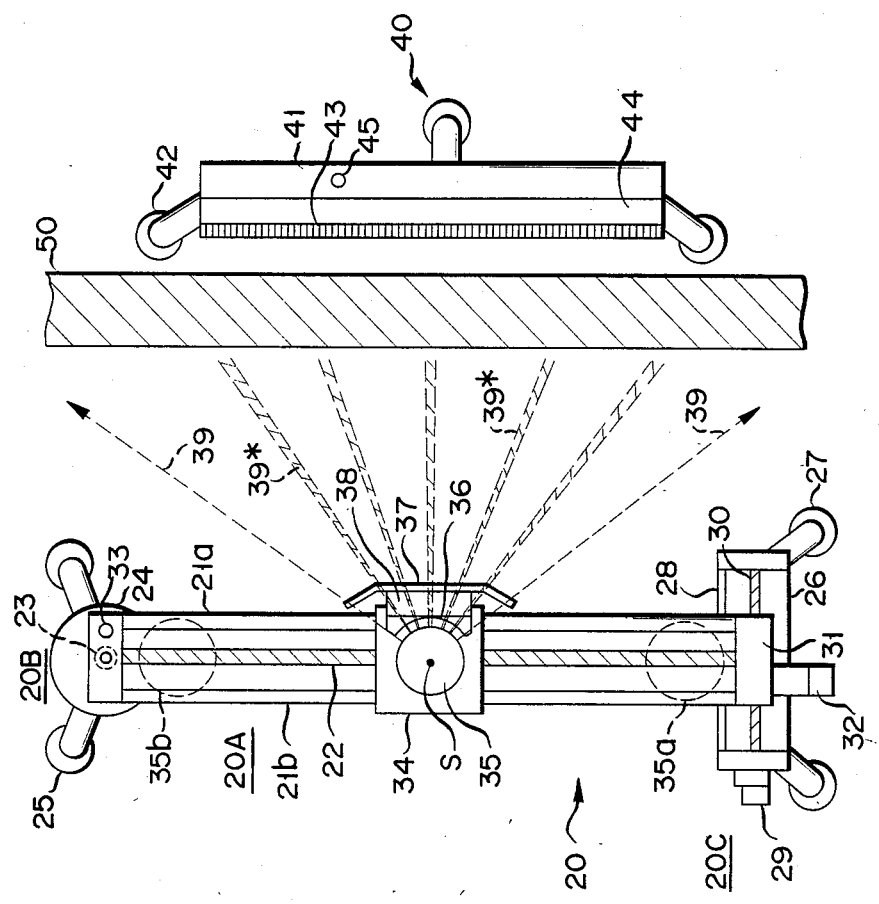
FIG. 1 illustrates an upper-side view of the mechanical part of a tomographic apparatus according to an embodiment of the invention.

FIG. 1 illustrates an upper-side view of the mechanical part of a tomographic apparatus according to an embodiment of the invention. A radiation generator system 20 faces a radiation sensor system 40. An object 50, e.g., a part of a large construction object 50, is located between the systems 20 and 40. The location of sensor system 40 can be set independently from the location of generator system 20.

Radiation generator system 20 is formed with a pair of guide rails 21a and 21b which are parallel to each other. A scan drive screw 22 is provided between guide rails 21a and 21b. Guide rails 21a, 21b and drive screw 22 constitute a scan locus mechanism 20A. One end of mechanism 20A is pivotally supported at a rotary shaft 23 of a rotor support mechanism 20B. The other end of mechanism 20A is made movable by means of a locus position adjusting supporter 20C, so that scan locus mechanism 20A can rotate around rotor shaft 23.

Rotor support mechanism 20B includes a base member 24 which may have a disc-like shape. Rotor shaft 23 is projected from the center of the disc-like base member 24. Base member 24 is provided with a lift mechanism (not illustrated) which allows up/down motion of member 24. Member 24 is mounted on a fixing pad 25. By means of pad 25, mechanism 20B is set at a given height position over a floor on which pad 25 is placed.

Locus position adjusting supporter 20C includes a base member 26 whose section may have a square-notched shape. Base member 26 may also be provided with a lift mechanism. Member 26 is mounted on a fixing pad 27, so that mechansim 20C is set at a given height over the floor. A drive screw 30 is provided between the square notch of member 26. Screw 30 is rotated by means of a locus correction driver 29. Also provided between the square notch of member 26 is a guide rail 28 arranged in parallel to screw 30.

Drive screw 22 is rotated by means of a scan driver 31. Driver 31 is coupled to guide rails 21a and 21b, and is movably mounted on screw 30. Thus, scan locus mechanism 20A is shifted (rotated) with the rotation of screw 30. The number of turns of screw 22 is detected by a rotary encoder 32. The horizontal level of radiation generator system 20 is monitored by a leveling instrument 33.

A scanner frame 34 is movably mounted on guide rails 21a and 21b. Scanner frame 34 is provided with a radiation generator 35 which may be formed of an X-ray tube or the like. Frame 34 is engaged with scan drive screw 22, and frame 34 can be shifted along guide rails 21a and 21b by means of scan driver 31 via the rotation of screw 22.

In front of the radiating outlet of generator 35, a reference detector 36 for measuring the radiation intensity, and a collimator plate 37 formed of a plurality of pinholes (or slits), are placed at respective prescribed locations. Collimator plate 37 is movable by means of a collimator driver 38. When plural pencil beams 39* are utilized to obtain a CT image of object 50, driver 38 lifts collimator plate 37 up so that plate 37 is inserted in the radiation path of fan beams 39 generated from radiation generator 35. When the fan beam radiation is used for the inspection, driver 38 lowers collimator plate 37 so that plate 37 is removed from the radiation path.

Radiation sensor system 40 is formed with a support base 41 having a predetermined length along object 50. Support base 41 may be provided with a lift mechanism, if required. Base 41 is mounted on a fixing pad 42, so that sensor system 40 is set at a given height over the floor. A radiation sensor 43 and a data collector 44 are mounted on support base 41. Radiation sensor 43 is formed of a plurality of sensor elements, each of which electrically converts the intensity of sensed radiation into radiation absorption data. The converted radiation absorption data from each sensor element is collected by data collector 44. Support base 41 is also provided with a leveling instrument 45 for monitoring the horizontal level of radiation sensor system 40.

Figure 2:
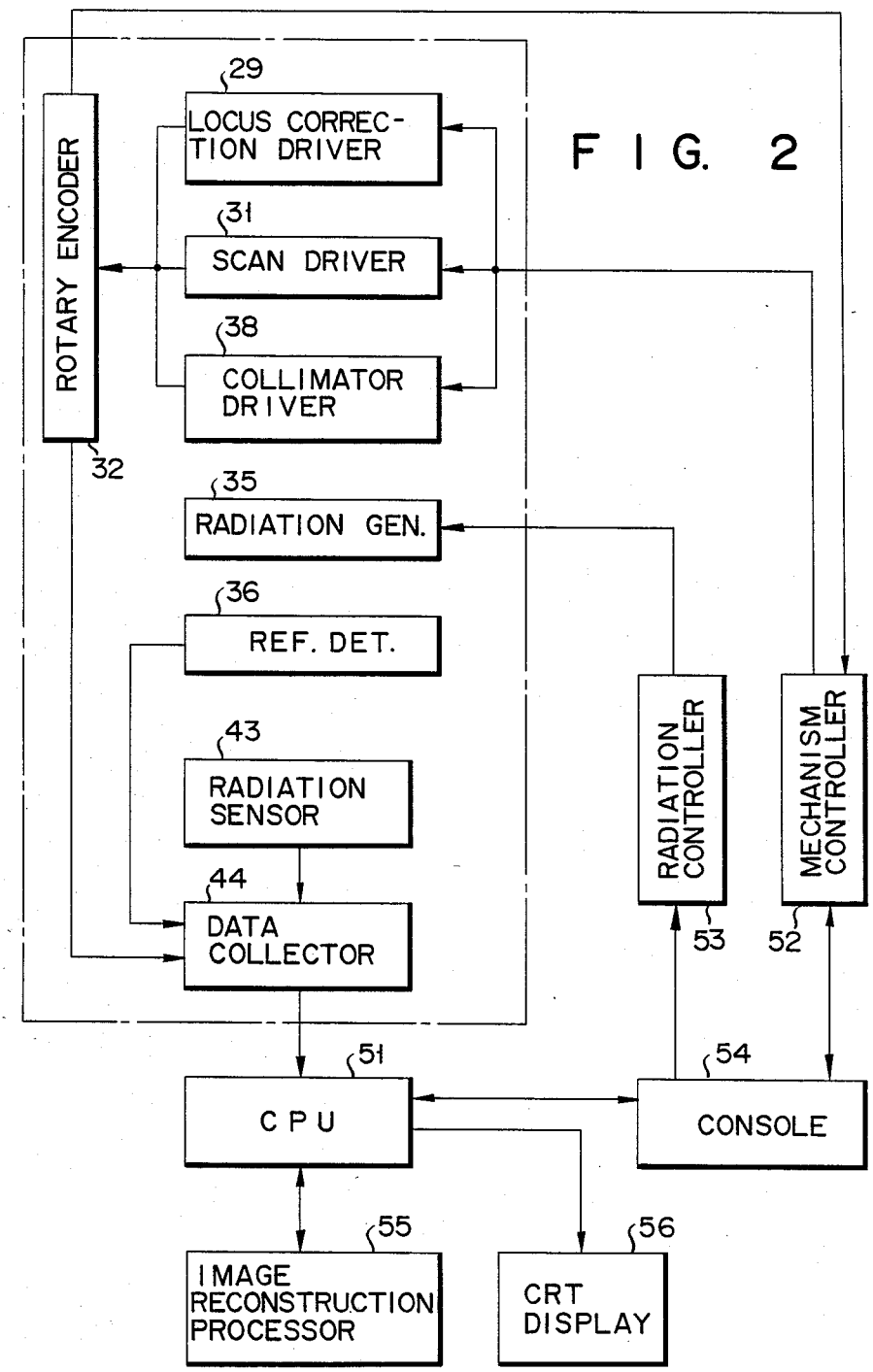
FIG. 2 shows a block configuration of the electrical part of the tomographic apparatus according to the embodiment.

FIG. 2 shows a block configuration of an electrical part of the tomographic apparatus. Encoder 32, reference detector 36 and radiation sensor 43 are coupled via data collector 44 to a microcomputer 51 (hereinafter referred to as CPU 51). Also coupled to CPU 51 are an image reconstruction processor 55 and a CRT display 56. Processor 55 may be a conventional one as disclosed in Japanese Patent Disclosure No. 53-96689. The output form encoder 32 is a pulse signal representing the scanning position of radiation generator 35. (This pulse signal corresponds to the number of turns of scan drive screw 22.) CPU 51 is controlled by instructions delivered from a console 54. Other instructions from console 54 are supplied to a mechanism controller 52 and to a radiation controller 53.

Mechanism controller 52 governs the operation of locus correction driver 29 and collimator driver 38. If necessary, controller 52 controls the up/down motions of radiation generator system 20 and radiation sensor system 40. Also, controller 52 receives the pulse signal from encoder 32 and controls scan driver 31, so that scanner frame 34 is shifted according to the received pulse signal.

Radiation controller 53 governs the operation of radiation generator 35 so that generator 35 provides the X-ray radiations continuously or intermittently.

Before starting the operation of FIG. 2 configuration, radiation generator system 20 and radiation sensor system 40 are arranged roughly in parallel to the longitudinal direction of object 50. At this time, generator and sensor systems 20 and 40 are set at a prescribed height over the floor. This height setting may be achieved by a conventional manner. For instance, a screw member is adapted to each support member (not shown) of systems 20 and 40, and this screw member is manually turned by means of a handle (not shown). Alternatively, such a screw member may be adapted to each of fixing pads 25, 27 and 42.

Of course, the above height setting may be effected automatically by means of a conventional servo control. For instance, a screw drive motor (not shown) engaged with the above screw member is operated according to a given height control instruction supplied from console 54 to mechanism controller 52, so that the height of each of systems 20 and 40 approaches the given target height of the servo control.

With the above height setting, the horizontal level of each of generator and sensor systems 20 and 40 is adjusted with the aid of leveling instruments 33 and 45, so that the plane of radiation containing the shifting locus of generator 35 passes through the linear arrangement of sensor elements in radiation sensor 43. Such an adjustment can be easily achieved when two crossing level vials are employed for each of leveling instruments 33 and 45.

Incidentally, so long as the above radiation plane passes the linear sensor elements, generator and sensor systems 20 and 40 may be slanted with respect to the floor.

After completion of the above height adjustment, a fine parallel adjustment between radiation generator system 20 and radiation sensor system 40 is performed. This fine parallel adjustment may be automatically effected by means of a sequence control of a microcomputer. For instance, when a start instruction of the sequence control is supplied from console 54 to mechanism controller 52, controller 52 renders the collimation driver 38 active, so that collimator plate 37 is inserted into the radiation path of fan beams 39. Then, fan beams 39 are converted into multi-pencil beams 39* via the pinholes (slits) of collimator plate 37. These converted pencil beams 39* are detected by respective sensor elements of radiation sensor 43.

While continuing the radiation of multi-pencil beams 39*, the location of radiation generator 35 is shifted from one end position 35a of guide rails 21a and 21b to the other end position 35b thereof by the actuation of scan driver 31. During the above shifting of generator 35, radiation sensor 43 supplies radiation absorption data to CPU 51 via data collector 44. CPU 51 stores data of a distance (l1 shown in FIG. 8) between the radiation generating point S of generator 35 and the collimator plate 37. CPU 51 also stores data of the pitch (d1 in FIG. 8) of the pinholes (or slits) of collimator plate 37. The pitch of pencil beams 39* can be calculated from the detection result of beams 39* by means of radiation sensor 43.

From the above distance data, pinhole pitch data and pencil beam pitch data, how generator system 20 and sensor system 40 deviate from an exact parallel arrangement can be known. Thus, CPU 51 detects the direction of the above deviation from the parallel arrangement, and calculates the amount of the deviation occurring during the shift of generator 35 from position 35a to position 35b. (This will be described in detail with reference to FIG. 9).

Obtained data of the direction and amount of deviation from the parallel is used for the fine parallel adjustment between generator and sensor systems 20 and 40. Thus, CPU 51 supplies the above parallel deviation data to console 54, so that mechanism controller 52 controls locus correction driver 29 based on this deviation data. By the operation of driver 29, screw 30 rotates in a prescribed direction according to the contents of the deviation data, so that scan locus mechanism 20A rotates slightly around rotor shaft 23 and the amount of deviation from the parallel is minimized. This deviation minimizing operation is continued until the accuracy of the parallel relation between systems 20 and 40 becomes satisfactory.

After completion of the fine parallel adjustment between systems 20 and 40, collimator driver 38 is instructed by mechanism controller 52, so that collimator plate 37 returns to its rest position. Then, the radiation of fan beams 39 is freed from collimator plate 37. Namely, fan beams 39, not pencil beams 39*, are radiated toward radiation sensor 43.

Figure 3:
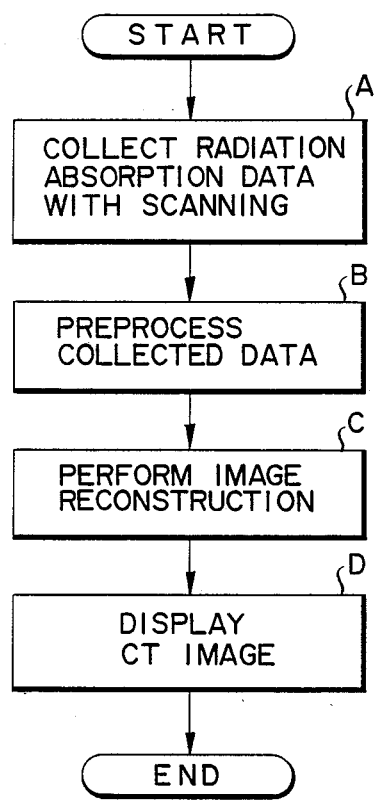
FIG. 3 is a general flow chart summarizing the whole operation of the embodiment.

Thereafter, main scanning for obtaining the CT image of object 50 is performed. The control sequence of the main scanning and of the processing for data collected during the main scanning is summarized in the general flow chart of FIG. 3. Thus, after starting the apparatus operation, radiation absorption data is collected with traversal scanning of the X-ray radiation (step A). The collected data is preprocessed in a known manner (step B). The preprocessed data is reconstructed (step C). Then, the CT image of object 50 is obtained from the reconstructed data (step D). Details of each of these steps A to D are as follows.

A. Traversal Scanning and Data Collection

First, console 54 provides an operation start instruction. Mechansim controller 52 controls the operation of scan driver 31 in response to the operation start instruction, so that radiation generator 35 is initially located at scan start position 35a. This initial location of generator 35 is detected by rotary encoder 32, and the detected initial location is informed via data collector 44 to CPU 51. Then, CPU 51 informs console 54 of the fact that radiation generator 35 is located at scan start position 35a. Following this, console 54 supplies respective circuit elements 51 to 53 with instructions for starting the scanning.

Incidentally, after elapsing a certain period of time from the generation of the operation start instruction, console 54 may supply the above scan start instructions, without confirming whether or not the radiation generator 35 is actually located at scan start position 35a.

Generally speaking, console 54 is provided with the function of supplying an instruction obtained from the manipulation of an apparatus operator to internal circuits of the tomographic apparatus, and the function of informing the apparatus operator of the operational conditions of the internal circuits by means of, e.g., indicator lamps. Thus, console 54 serves as an interface for CPU 51 and respective controllers 52 and 53. CPU 51 controls the internal circuits with a prescribed timing according to a given sequence control program adapted to CPU 51, except for the operation start initiated by the operator's manipulation through console 54. (Of course, console 54 may control the internal circuits according to another sequence control program adapted to console 54.)

In the following, explanation will be given of a case where the tomographic apparatus is controlled in accordance with the sequence control program of CPU 51. When CPU 51 generates a scan start instruction according to the sequence control program, this instruction is supplied via interfacing console 54 to controllers 52 and 53. Radiation controller 53 responds to this instruction and supplies an intermittent or continuous current with a high voltage potential to radiation generator 35, so that generator 35 radiates fan beams 39 toward object 50. On the other hand, when the above instruction is received by mechanism controller 52, controller 52 supplies certain drive power to scan driver 31. Then, scan drive screw 22 rotates in a defined direction with a given rotation speed, so that radiation generator 35 shifts, with a certain (generally) constant speed, from scan start position 35a toward scan end position 35b.

The rotation of scan drive screw 22 is detected by encoder 32. Thus, encoder 32 generates pulse signals representing the shift of generator 35. These pulse signals are supplied to data collector 44 and to mechanism controller 52. Controller 52 detects the scan position of generator 35 by counting the pulse signals from encoder 32. Scan position data obtained by this counting is supplied via console 54 to CPU 51.

While receiving the pulse signals from encoder 32, data collector 44 integrates, in accordance with the generation timing of the pulse signals, the radiation absorption data obtained from each of the sensor elements in radiation sensor 43. Then, data collector 44 supplies the integrated absorption data to CPU 51. The train of the above pulse signals indicates the start and the end of the data integration performed in collector 44. CPU 51 is provided with a disc memory (not shown) for sequentially storing the integrated absorption data in synchronism with the generation timing of the pulse signals.

Figure 4:
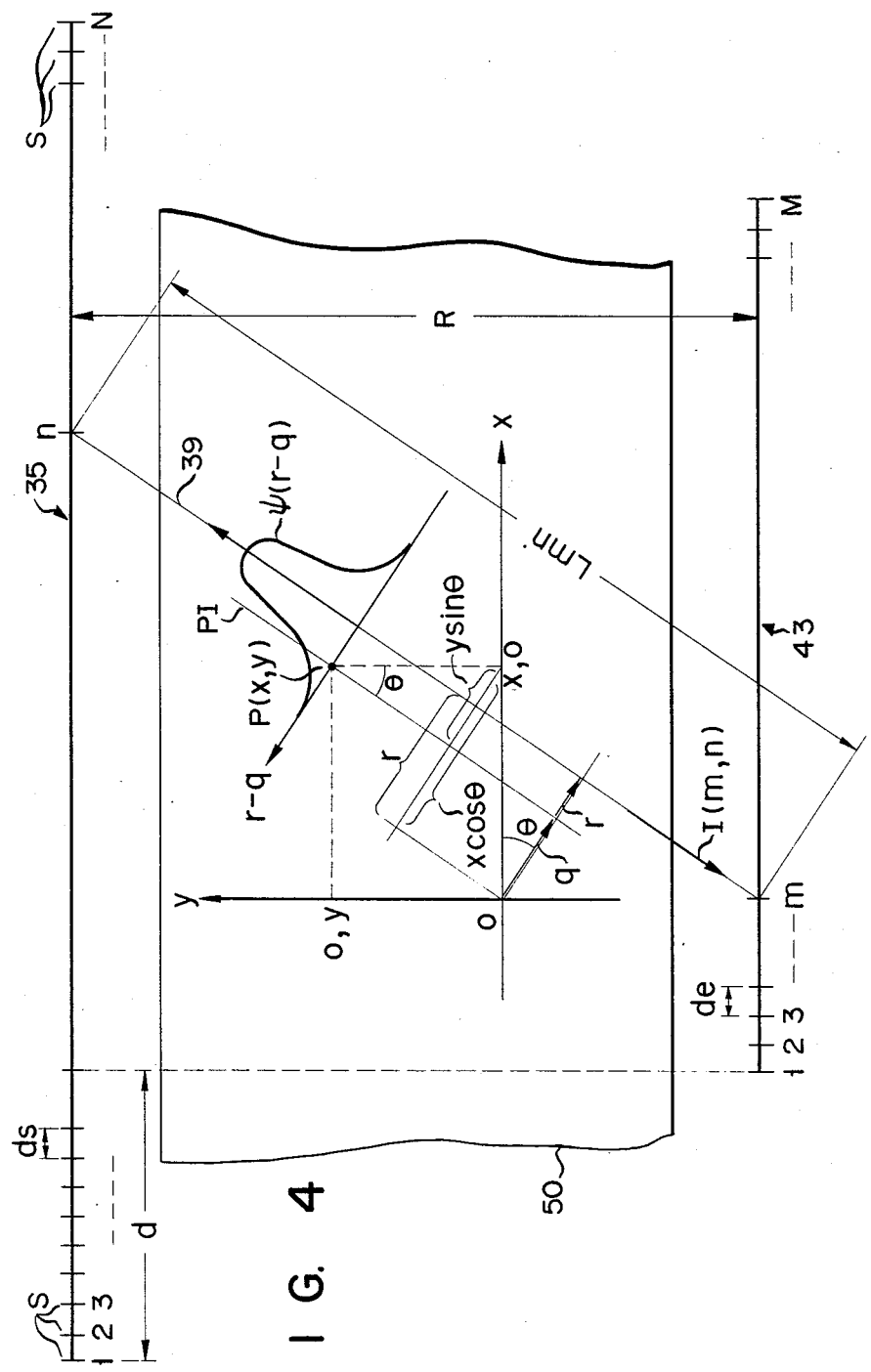
FIG. 4 shows the geometrical relationship between the radiation generating point (n) and the radiation sensing point (m) of the FIG. 1 embodiment.

Each data integrated in data collector 44 represents data obtained from each of serially arranged radiation generating points S (FIG. 4). This is because the pulse signals from encoder 32, which are supplied to data collector 44, are generated in correspondence to the amount of shift of radiation generator 35. Each of the above generating points S equivalently appears at the intermediate point of the shifting step of radiation generator 35, which shifting step is formed during the period of each integrating operation of data collector 44.

FIG. 4 illustrates the geometrical relationship between each radiation generating point S and each radiation sensing point. In the figure, the upper line indicates the locus of point S of radiation generator 35, which is equally divided by N radiation generating points S, while the lower line indicates the arrangement of radiation sensor 43, which is equally divided by M radiation sensing points. These radiation sensing points are located at respective intermediate portions of the sensor elements in radiation sensor 43.

Each radiation beam 39 from generating points 1, 2, 3, ..., N passes through object 50. Each of these beams 39, passing through object 50, is sensed by one of the sensor elements of radiation sensor 43. One sensor element can be defined by the radiation generating point and the angle of tilt of beam 39.

Assume that a radiation beam generated from the nth radiation generating point is sensed at the mth radiation sensing point. The radiation path of such a beam is denoted as I(m,n). In this case, X-ray absorption data Imn of radiation beam path I(m,n) may be specified by the generating point n and sensing point m. Namely, respective radiation absorption data Imn among each of N generating points and each of M sensing points are specified for each of radiation generating points 1, 2, 3, ..., N.

Incidentally, the horizontal displacement d between radiation generator 35 and radiation sensor 43, and the vertical distance R between generator 35 and sensor 43 have already been obtained in the course of the fine parallel adjustment between systems 20 and 40.

B. Preprocessing for Collected Data

The stored integrated absorption data is read out from the disc memory of CPU 51. This read-out data is supplied to image reconstruction processor 55. (Details of the inner configuration of processor 55 will be described later.) In the following, how the preprocessing is effected on the read-out data will be described.

The preprocessing includes an offset correction for each of the radiation sensor elements, a sensitivity correction for each of the radiation sensor elements, a compensation for a change of the radiation intensity, a log-conversion, etc. The following description is directed with respect only to the preprocessing for absorption data Imn.

(1) Offset Correction for Sensor Elements

Assume that an output of the sensor element at sensing point m, which is obtained under no radiation, is Iom. Then, offset corrected data Imn* is:

$$Imn^* = Imn - Iom \qquad (1)$$

(2) Sensitivity Correction for Sensor Elements

Assume that the distance between radiation generating point n and radiation sensing point m is Lmn, the distance between points n and m obtained at the time of correction is Lo, and the offset corrected data of the sensor element of point m obtained at the time of correction is Im*. Then, sensitivity corrected data Imn* is:

$$Imn^{**} = (Lmn/Lo)^2 \cdot (Imn^*/Im^*) \cdot Kmn \qquad (2)$$

where Kmn is a correction coefficient with respect to radiation generating point n and radiation sensing point m. Such a coefficient Kmn is necessary because the radiation beam from point n to point m generally inclines with respect to the linear arrangement of the sensor elements. This correction coefficient Kmn is tabled in advance, and stored in the memory of CPU 51.

Incidentally, data Lo and Im* can be obtained according to the same manner as in the case of obtaining data Lmn and Imn*, except that object 50 is removed from the radiation path when data Lo and Im* are obtained in the correction operation.

(3) Compensation for Radiation Intensity

In this compensation, output data from reference detector 36 is used. Assume that the offset corrected data of a sensor element of detector 36, whose location is closest to beam path I(m,n), is IRmn*, and that the sensitivity correction factor of the above sensor element is (IRmn*)o. Then, radiation intensity corrected data Imn*** is:

$$Imn^{***} = [(IRmn^*)o/IRmn^*] \cdot Imn^{**} \quad (3)$$

Similar radiation intensity correction is disclosed in Japanese Patent Publication No. 54-36837 (EMI), or U.S. Pat. No. 4,069,422. All disclosures of this U.S. Patent are incorporated herewith.

(4) Log Conversion

Log-converted data $\tau m(m,n)$, i.e., preprocessed data $\tau m(m,n)$, is obtained according to the following relation:

$$\tau m(m,n) = -\ln(Imn^{***}) \quad (4)$$

and the obtained data $\tau m(m,n)$ is restored in the disc memory of CPU 51. Preprocessed data $\tau m(m,n)$ is obtained for each of radiation generating points 1, 2, 3, ..., N, and these obtained data $\tau m(m,n)$ are tabled in the disc memory of CPU 51.

C. Reconstruction of Preprocessed Data

After completing the preprocessing, the image reconstruction operation is effected. Thus, CPU 51 reads out preprocessed data $\tau m(m,n)$ of each pixel of the CT image from the disc memory, and sends the read-out data to image reconstruction processor 55. In processor 55, the image reconstructing operation is performed based on a sequential approximation method. A similar method is disclosed in Japanese Patent Publication No. 52-1274 (EMI), or U.S. Pat. No. 3,867,634. All disclosures of this U.S. Patent are incorporated herewith. According to the sequential approximation method, a weight function depending on a reliability of data for the radiation beam path I(m,n) is utilized, so that the reconstructed image avoids influence of quantum noise.

How the sequential approximation method is employed will be described below referring to the flow of FIG. 5.

According to the sequential approximation method, each data of the pixels of the CT image is sequentially read out from the disc memory table, and actual CT values of the respective pixels are calculated in order. To be concrete, initial image data $\mu(x,y) = \mu o$ (constant) is present (step S1 in FIG. 5). The value of initial preset image data $\mu o$ is properly determined under an assumption that the CT values of object 50 are wholly the same regardless of the material thereof. This present data $\mu o$ is used for calculating the gradient g of an estimation funtion J (step s2). (Details of the function of g will be described later.)

In step S2, a reference value Jo for the estimation function J is provided, and the direction and degree of the gradient g is calculated in accordance with initial image data $\mu o$ and reference value Jo. Based on the calculated direction and degree of gradient g, the direction $S_i(x,y)$ for the image correction is calculated (step S3). (Details of the function of $S_i(x,y)$ will be described later).

Then, an intial amount $\alpha o$ of direction $S_i(x,y)$ is preset for a correction amount $\alpha$ (step S4). Following to this, initial corrected image data $\mu_{i+1}(x,y)$ is provisionally calculated (step S5). This initial corrected image data $\mu_{i+1}(x,y)$ is estimated according to the estimation function $J[\mu(x,y)]$ (step S6).

Figure 5:
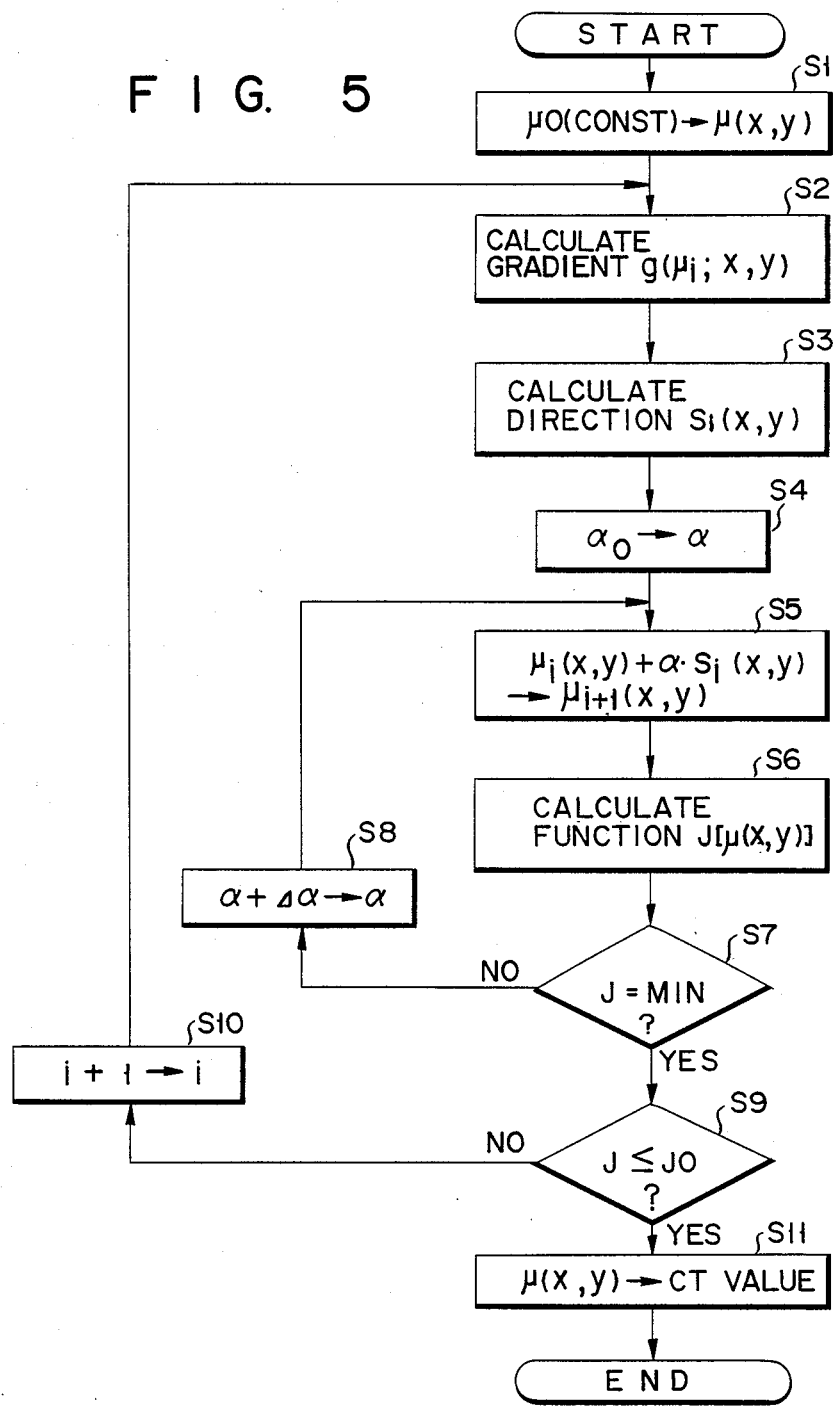
FIG. 5 is a flow chart showing an image reconstruction process to which a sequential approximation method based on preprocessed data is applied.

Details of steps S2 to S6 of the flow in FIG. 5 are as follows.

It is known that estimation function $J[\mu(x,y)]$ for initial image data $\mu o$ is represented as:

$$J[\mu(x,y)] = \sum_m \sum_n w(m,n) \cdot |\tau m(m,n) - \tau[\mu(x,y):m,n]|^2 \quad (5)$$

With the approach of the calculation result of function J to the value of initial image data $\mu o$, the value of function J becomes small. From this, whether or not the value of estimation function $J[\mu(x,y)]$ has converged to the minimum is checked (step S7).

If estimation function $J[\mu(x,y)]$ does not reach the minimum value (NO at step S7), correction amount $\alpha$ is incremented by $\Delta\alpha$ (step S8), and the program sequence is returned to step S5. Then, newly corrected image data $\mu_{i+1}(x,y)$ is calculated in step S5, and the corresponding new estimation funtion $J[\mu(x,y)]$ is calculated in step S6. If estimation function $J[\mu(x,y)]$ reaches the minimum value (YES at step S7), the calculated minimum funtion J is compared with the reference value Jo (step S9). Reference value Jo may be obtained in advance, with the use of a test phantom, or according to preliminary experience.

If the value of function $J[\mu(x,y)]$ is not less than Jo (NO at step S9), the incrementing parameter i of corrected image data $\mu_{i+1}(x,y)$ is incremented by 1 (step S10), and the program sequence is returned to step S2. Then, through steps S2 to S8, new gradient g, new direction $S_i$ and new minimum estimation function J are calculated for the new incremented parameter i. If the value of newly calculated function J is equal to or less than Jo (YES at step S9), the calculated image data $\mu_{i+1}(x,y)$ is used for a true CT value (step S11).

Preprocessed data $\tau m(m,n)$ in Eq.(5) corresponds to the projection data of radiation absorption with respect to a given radiation path I(m,n). Further, $\tau[\mu(x,y):m,n]$ in Eq.(5) represents the projection data of radiation absorption with respect to radiation path I(m,n), which is obtained by a reverse operation from initial image data $\mu(x,y) = \mu o$ based on the following relation:

$$\tau[\mu(x,y):m,n] = \sum_x \sum_y \psi(r - q) \cdot \mu(x,y) \quad (6)$$

In Eq.(6), the function $\Psi(r-q)$ indicates an intensity of radiation beam of I(m,n) with respect to a distance parameter $(r-q)$. The origin of function $\Psi(r-q)$ is on radiation beam path I(m,n), as shown in FIG. 4. (In an actual calculation, function $\Psi(r-q)$ may be simplified for convenience.) The parameter $(r-q)$ represents the distance between radiation path I(m,n) and a position P(x,y) of a target pixel located on the corresponding radiation path PI of object 50. (Path PI is parallel to path I(m,n), and passes through position P(x,y) with an inclination $\theta$ from the y axis of the x-y plane defined in the object 50. The x axis of this x-y plane is generally set to be parallel to the linear arrangement of radiation sensor 43.)

$\tau[\mu(x,y):m,n]$ of Eq.(6) may be regarded as converted projection data of initial image data $\mu(x,y)$, which is modified in accordance with function $\Psi(r-q)$.

The relation between the position P(x,y) of the pixel of initial image data $\mu o$ and the radiation beam path I(m,n), is shown in FIG. 4. The parameters q, $\theta$ and r indicated in FIG. 4 may be represented as:

$$q = x \cos o - y \sin o \\ \theta = \theta(m,n) \\ r = r(m,n) \Bigg\} \quad (7)$$

Thus, function $\Psi(r-q)$ can be regarded as the function of parameters x, y, m and n. In conclusion, it can be said that $\tau[\mu(x,y):m,n]$ of Eq.(6) represents the projection data obtained when initial image data $\mu(x,y)$ is projected onto radiation beam path $I(m,n)$.

Weight function $w(m,n)$ in Eq.(5) modifies the estimation of path $I(m,n)$. In other words, Eq.(5) shows a weighted estimation represented by the method of least squares. Function $w(m,n)$ depends on the value of preprocessed projection data $\tau m(m,n)$. That is, a large weighting value is assigned to function $w(m,n)$ if a high S/N ratio is obtained for data $\tau m(m,n)$, while a small value weight function $w(m,n)$ is used for a low S/N preprocessed projection data $\tau m(m,n)$.

The following relation may be used for weight function $w(m,n)$:

$$w(m,n) = \sqrt{Imn^{***}} = \sqrt{\exp[-\tau m(m,n)]} \quad (8)$$

According to the relation of Eq.(8), the value of function $w(m,n)$ roughly proportional to the S/N ratio of preprocessed projection data $\tau m(m,n)$.

The relation between weight function $w(m,n)$ and radiation intensity corrected data $Imn^{*}$ may be different from Eq.(8). For instance, a relation $w(m,n) = k \cdot Imn^{*}$ (k is a proportional constant) may be utilized to determine the value of weight function $w(m,n)$.

According to the above-mentioned sequential approximation method, the apparatus control is effected to minimize the value of estimation function J by repeating, with a slight progressive change of $\Delta\alpha$, the image correction operation for initial image data $\mu(x,y)$, in accordance with the relation of Eq.(5).

More detailed sequence of FIG. 5 will be described below, under the assumption that an initial image data $\mu(x,y)$ has been estimated by i times, that the estimation function $J[\mu_i(x,y)]$ for the above image data $\mu_i(x,y)$ has been converged to the minimum value (YES at step S7 in FIG. 5) but the minimum value of this function J has exceeded the reference value Jo (NO at step S9), that the program sequence has been returned to step S2 via the incrementing step S10, and that corrected image data $\mu_{i+1}(x,y)$ for the (i+1)th sequence is to be performed.

The rate of change of the first order with respect to the ith estimation function $J[\mu_i(x,y)]$ may be represented as:

$$\delta J[\mu_i(x,y)] = \sum_x \sum_y g[\mu_i(x,y):x,y] \cdot \delta\mu_i(x,y) \quad (9)$$

In Eq.(9), $J[\mu_i(x,y)]$ is functional to the term $\mu_i(x,y)$. The term $g[\mu_i(x,y):x,y]$ represents the gradient of function J at $\mu_i(x,y)$ (ith iterated image data), and is obtained according to the rate of change of function J in Eq.(5) with respect to $\mu_i(x,y)$:

$$g[\mu_i(x,y):x,y] = 2 \sum_m \sum_n w(m,n) \cdot \{\tau m(m,n) - \tau[\mu_i(x,y):m,n]\} \cdot \psi(r-q) \quad (10)$$

Thus, the gradient g of step S2 (FIG. 5) can be obtained according to Eq.(10).

It should be noted that the estimation function J can be minimized effectively, by changing the correction amount $\alpha$ for the direction of $g[\mu_i(x,y):x,y]$ when $(i+1)$th image data $\mu_{i+1}(x,y)$ is obtained from the preceding image data $\mu_i(x,y)$. When the rate of convergence of function J for obtaining its minimum value is high, the Fletcher-Reeves's algorithm, which is a conjugate gradient method, may be utilized. This algorithm is disclosed in:

NUCLEAR INSTRUMENTS AND METHODS IOI (1972) (NORTH-HOLLAND PUBLISHING CO.) "THREE-DIMENSIONAL DENSITY RECONSTRUCTION FROM A SERIES OF TWO-DIMENSIONAL PROJECTIONS", (PP 509–518) WRITTEN BY M. GOITEIN.

According to the Fletcher-Reeve's algorithm, the image correcting direction $S_i(x,y)$ for $\mu_i(x,y)$ to be calculated in step S3 of FIG. 5 is:

$$S_i(x,y) = g[\mu_i(x,y):x,y] + \{||g[\mu_i(x,y):x,y]||^2/||g[\mu_{i-1}(x,y):x,y]||^2\} \cdot S_{i-1}(x,y) \quad (11)$$

After calculating the direction $S_i(x,y)$ according to Eq.(11), given correction amount $\alpha_i$ for direction $S_i(x,y)$ is applied to change the preceding corrected image data $\mu_i(x,y)$, so that the following newly corrected image data $\mu_{i+1}(x,y)$ is obtained:

$$\mu_{i+1}(x,y) = \mu_i(x,y) + \alpha_i \cdot S_i(x,y) \quad (12)$$

Renewed estimation function J is then calculated according to Eq.(5), with linear searching and based on the above new image data $\mu_{i+1}(x,y)$.

The calculation for obtaining data $\mu_{i+1}(x,y)$ of Eq.(12) is repeated for several different correction amount $\alpha_i$ until the minimum value of estimation function $J[\mu_{i+1}(x,y)]$ is obtained.

Following this, new corrected image data $\mu_{i+2}(x,y)$ is similarly calculated in accordance with the preceding image data $\mu_{i+1}(x,y)$, and such a calculation is repeated until a certain estimation function J, which is smaller than reference value Jo, is obtained. When $J \leq Jo$ is obtained, the repetition (or iteration) of the above data processing is ended, and the finally obtained image data $\mu(x,y)$ is stored, as the true CT value, in the memory of CPU 51. Such data processing to obtain the true CT value is effected for each prescribed pixel of the CT image.

Figure 6:
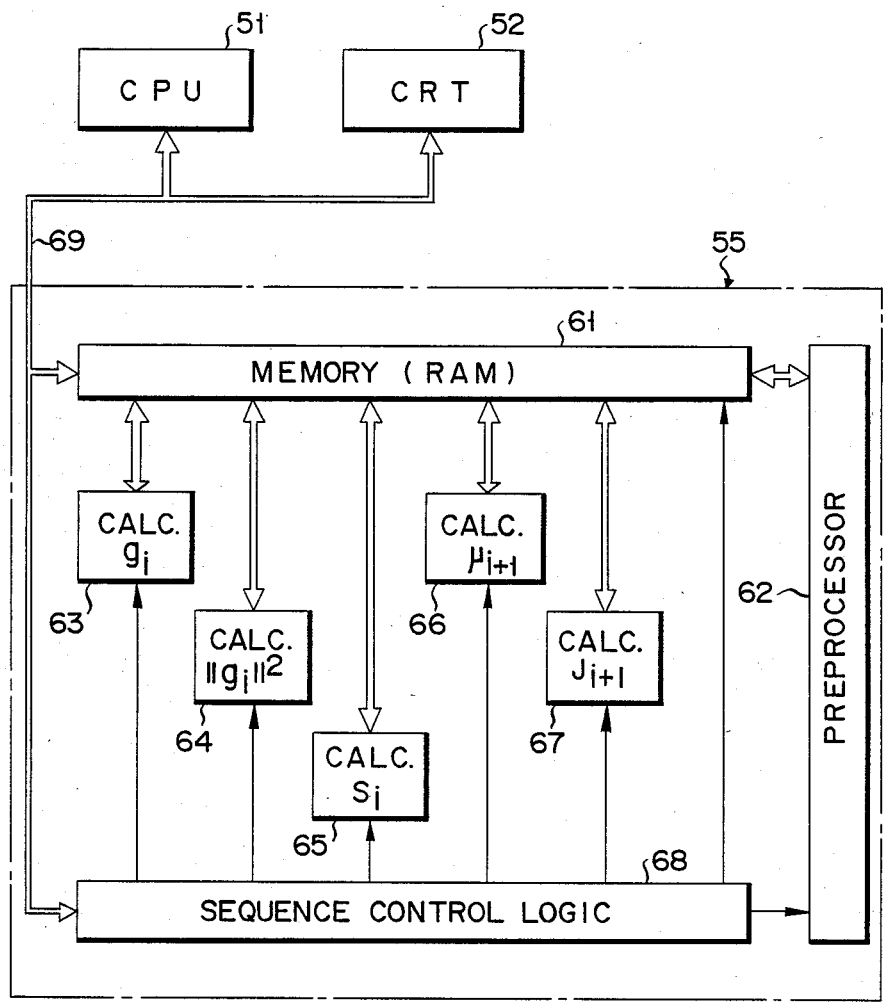
FIG. 6 shows details of the image reconstruction processor (55) used in FIG. 2.

Image reconstruction processor 55 in FIG. 2 may have a configuration as shown in FIG. 6. As shown in FIG. 6, CPU 51 is coupled via a data bus 69 to a read/write memory (RAM) 61 and to a sequence control logic unit 68. Memory 61 is coupled to a preprocessor 62 which may be a conventional one. Memory 61 is also coupled to a $g_i$ calculator 63, $||g_i||^2$ calculator 64, $S_i$ calculator 65, $\mu_{i+1}$ calculator 66, and $J_{i+1}$ calculator 67. Also, logic unit 68 is coupled to the above preprocessor 62 and calculators 63 to 67.

Figure 7:
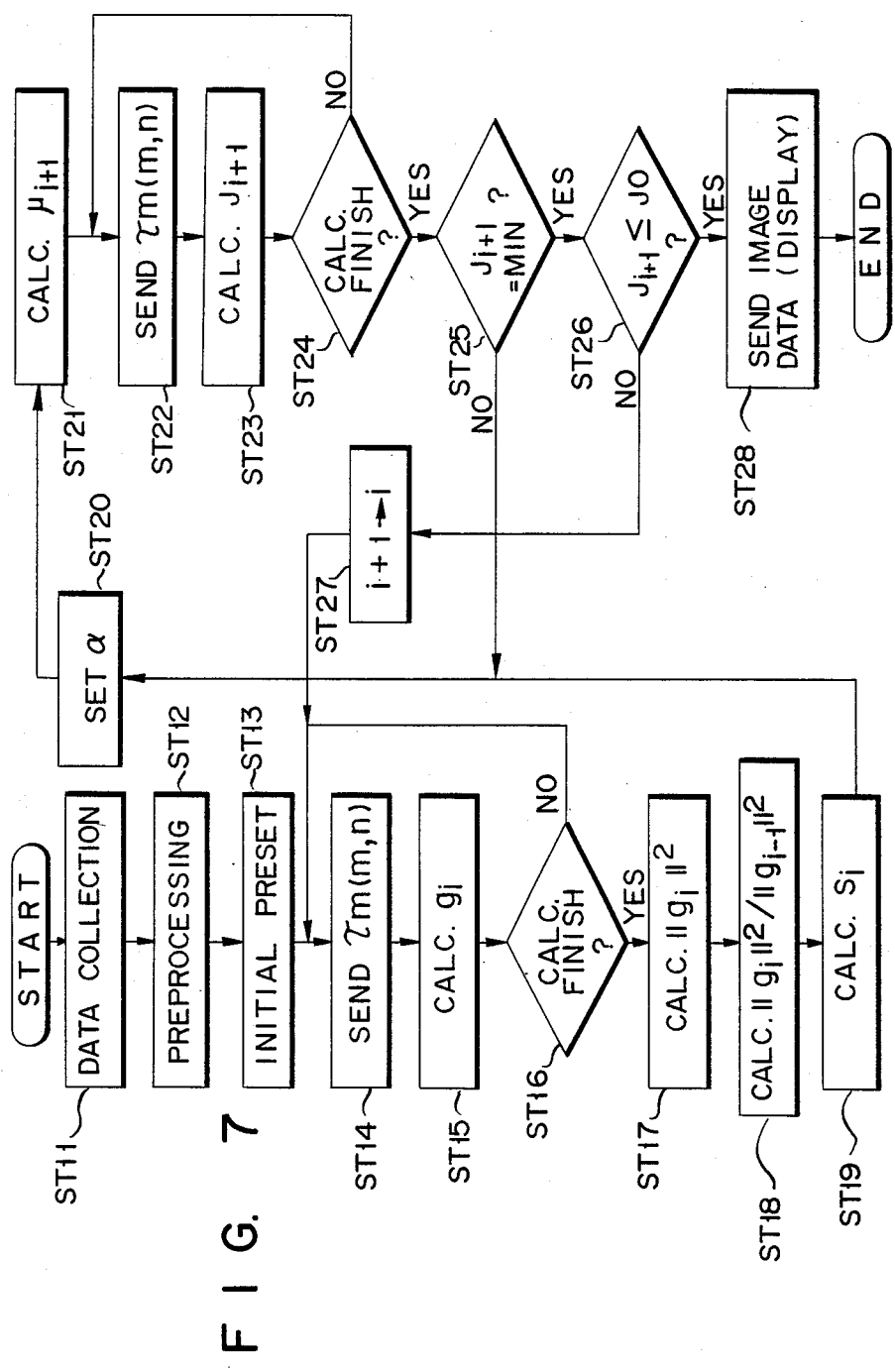
FIG. 7 is a flow chart showing the circuit operation of the image reconstruction processor (55) in FIG. 6.

The circuit operation of image reconstruction processor 55 will be described below with reference to the flow chart of FIG. 7. The radiation absorption data Imn is collected, and the collected data Imn is stored as projection data in the disc memory of CPU 51 (step ST11). Thereafter, CPU 51 supplies the obtained projection data Imn to memory 61 via bus 69. Projected data Imn stored in memory 61 is then sequentially read out from memory 61 under the sequence control of logic unit 68. The readout data Imn from memory 61 is supplied to preprocessor 62 by the control of logic unit 68, so that the aforementioned preprocessing (step A in FIG. 3) is effected (step ST12). Following this, the preprocessed data $\tau m(m,n)$ is sequentially restored in memory 61 according to the sequence control of logic unit 68.

When the preprocessing operation for all projection data Imn in the memory table of CPU 51 is completed, all preprocessed data $\tau m(m,n)$ are prepared. These preprocessed data $\tau m(m,n)$ are supplied from memory 61 to CPU 51 via bus 69 under the sequence control of logic unit 68.

Incidentally, if the contents (amount) of data Imn are so large that memory 69 overflows during the above preprocessing operation, data Imn may be suitably divided to avoid overflow.

After obtaining all projection data $\tau m(m,n)$ initial image data $\mu_0$ (constant) is set for initiating the said sequential approximation (step ST13). This initializing operation may be achieved in such a manner that CPU 51 sends the initial image data $\mu_0$ to memory 61. Then, the intial value of data $\mu_0$ is set in memory 61.

After the above initializing step, CPU 51 reads out the preprocessed projection data $\tau m(m,n)$ from the disc memory, and sends the readout data to memory 61 for calculating the gradient $g_i$ (step ST14). This calculation is achieved in calculator 63 (step ST15). If the memory capacity of memory 61 can not store all of data $\tau m(m,n)$, the steps ST14 and ST15 are effected on each suitably divided portions of data $\tau m(m,n)$, and the resultant gradient $g_i$ obtained by the calculation of calculator 63 is sequentially interchanged with the corresponding divided portion of preprocessed projection data $\tau m(m,n)$. The calculation of gradient $g_i$ is performed in accordance with the relation of Eq.(10), using the readout data $\mu_i(x,y)$ and $\tau m(m,n)$ from memory 61 (where $g_i$ is identical to $g[\mu_i(x,y):x,y]$ in Eq.(10)).

The above gradient $g_i$ calculation is repeated until all gradients $g_i$ for preprocessed projection data $\tau m(m,n)$ are obtained (NO at step ST16). When all gradients $g_i$ are obtained (YES at step ST16), the program sequence gets away from the loop of steps ST14 to ST16, and all of the obtained gradients $g_i$ are stored in memory 61.

After obtaining all gradients $g_i$, data of $g_i$ is sequentially read out from memory 61, and the calculation of $$||g_i||^2 \left( = \sum_x \sum_y \{g[\mu_i(x,y):x,y]\}^2 \right)$$

is performed in calculator 64, and then the result of the calculation of $||g_i||^2$ is returned to memory 61 (step ST17). (With the calculation of $||g_i||^2$, data of $||g_{i-1}||^2$ is also obtained, of course.)

After obtaining all $||g_i||^2$ data, data of $||g_i||^2$ and $||g_{i-1}||^2$ are sequentially read out from memory 61, and the calculation of $||g_i||^2/||g_{i-1}||^2$ is performed in CPU 51 (step ST18). In CPU 51, the preceding data (e.g., $||g_1||^2$) is used as $||g_{i-1}||^2$ for the next data (e.g., $||g_2||^2$) calculation. The obtained data of all of $||g_i||^2/||g_{i-1}||^2$ are returned to memory 61 and stored therein.

The calculated data of $||g_i||^2/||g_{i-1}||^2$ as well as gradient data $g_i$ are sequentially read out from memory 61, and supplied to calculator 65. In calculator 65, the correcting direction $S_i$ is calculated, using the direction $S_{i-1}$ calculated earlier, according to Eq.(11) (step ST19). The calculated correcting direction $S_i$ will be used as new data of $S_{i-1}$ for the next calculation of $S_i$. Incidentally, the contents of data $S_{i-1}$ for the first (ith=1st) operation are generally set at zero. In the end, all calculated direction $S_i$ data are stored in memory 61.

After obtaining all correcting direction $S_i$ data, the amount of correction $\alpha$, which is used in the calculation of Eq.(12), is set (step ST20). The data of correction amount $\alpha$ is supplied from CPU 51 to memory 61. Then, memory 61 supplies data $\alpha$, $\mu_i$ and $S_i$ to calculator 66 according to the sequence control of logic unit 68. Following this, calculator 66 calculates $\mu_{i+1}$ according to the relation of Eq.(12) (step ST21). The calculated result of $\mu_{i+1}$ is sequentially stored in memory 61.

After obtaining all corrected image data $\mu_{i+1}(x,y)$, CPU 51 supplies log-converted projection data $\tau m(m,n)$ to memory 61 (step ST22). Following this, $\tau m(m,n)$ and $\mu_{i+1}(x,y)$ are supplied to calculator 67 according to the sequence control of logic unit 68. The estimation function $J_{i+1}$ of Eq.(5) is calculated in calculator 67 (step ST23). The operation of steps ST22 and ST23 is repeated until the calculation of function $J_{i+1}$ for all projection data $\tau m(m,n)$ is completed (NO at step ST24), and the calculated function $J_{i+1}$ thus obtained is stored in memory 61. (If memory 61 cannot store all projection data $\tau m(m,n)$, the operation of steps ST22 to ST24 may be partially and sequentially effected on prescribed divided portions of data $\tau m(m,n)$, and the partially calculated function $J_{i+1}$ may be stored in memory 61 in order, so that overflow is prevented.)

When all calculations for estimation function $J_{i+1}$ are completed (YES at step ST24), whether or not the calculated function $J_{i+1}$ has the minimum value for the set data $\alpha$, is checked. If the calculated function $J_{i+1}$ is not minimum (NO at step ST25), the program sequence is returned to step ST20. Then, a new correction amount $\alpha + \Delta\alpha$ is set in place of the preceding correction amount $\alpha$, and the operation of steps ST21 to ST25 is done.

If the calculated function $J_{i+1}$ is minimized (YES at step ST25), whether or not the obtained minimum function $J_{i+1}$ is smaller than reference value Jo, is checked. If $J_{i+1}$ exceeds Jo (NO at step ST26), the repeating (or iterating) parameter i is incremented by 1 (step ST27), and the program sequence is returned to step ST14. Then, steps ST14 to ST27 are repeated until the calculated function $J_{1+1}$ falls under reference value Jo. When $J_{i+1}$ becomes less than Jo (YES at step ST26), the corrected image data $\mu_{i+1}$ for the minimum $J_{i+1}$ is used as the true CT value.

The image data $\mu_{i+1}$ obtained as the true CT value is read out from memory 61, and then stored in the disc memory of CPU 51. Also, this image data $\mu_{i+1}$ of the true CT value is sent to CRT display 52, so that data $\mu_{i+1}$ is stored in an image memory (not shown) adapted to CRT display 52 (step ST28). Then, CRT 52 displays the CT image of object 50 according to the above image data $\mu_{i+1}$.

An initial correction with respect to the dimensional relationship between the radiation generating point S and the pinhole (or slit) of collimator plate 37 will be described below with reference to FIG. 8.

It is sufficient to perform such an intial correction once when an X-ray tube of radiation generator 35 is exchanged, or when the mounting of collimator plate 37 is readjusted.

Figure 8:
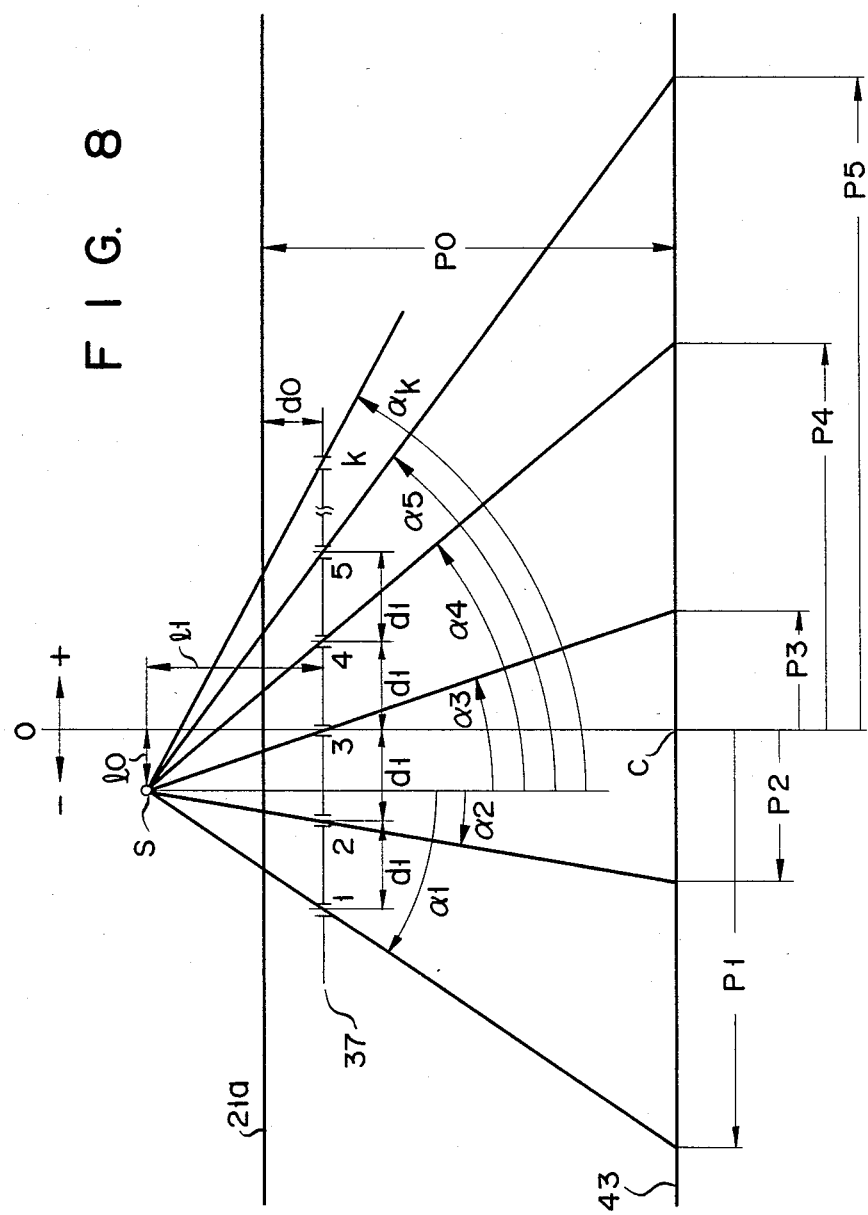
FIG. 8 illustrates the dimensional relationship between the radiation sensing point (S) and the pinhole (slit) of the collimator plate (37) shown in FIG. 1, which is useful to explain an intial correction for the tomographic apparatus.

FIG. 8, the symbol do denotes the distance between guide rail 21a and collimator plate 37, and the symbol d1 denotes the pitch of the pinholes (slits) of collimator plate 37. The values of do and d1 are prefixed according to the design of the apparatus. The symbol Po denotes the distance between guide rail 21a and radiation sensor 43. The value of Po may be measured with a use of a proper jig. The symbol C denotes a reference center position on the linear sensor arrangement of sensor 43, which passes perpendicularly through the third pinhole of collimator plate 37.

The symbol $\alpha 1$ denotes the angle of tilt of a pencil beam passing through the first pinhole of collimator plate 37. The symbol P1 denotes the distance between the position C and the cross point of the first pinhole pencil beam and the linear arrangement of sensor 43. Similarly, the symbols $\alpha 2$, $\alpha 3$, $\alpha 4$, ..., $\alpha_k$ respectively denote the tilt angles of pencil beams passing through the second to kth pinholes of collimator plate 37. The symbols P2, P3, P4 and P5 denote the distances between the position C and the respective cross points of the second to fifth beams and the linear sensor arrangement of sensor 43.

The symbol lo denotes the distance between a line passing the sensor perpendicularly through center position C and the position of radiation generating point S. The symbol l1 denotes the distance between the point S and collimator plate 37.

In FIG. 8, the right side of the vertical line on center position C is defined as a positive region, while the left side thereof is defined as a negative region.

The dimensions l1 and lo indicated in FIG. 8 can be obtained from the following relation:

$$l1 = 4d1(Po - do)/(P5 - P1 - 4d1) \qquad (13)$$

$$lo = -l1 \cdot P3/(Po - do) \qquad (14)$$

The values l1 and lo obtained according to Eqs.(13) and (14) are stored in the memory of CPU 51.

A deviation from the parallel between the locus of radiation generating point S and the linear arrangement of radiation sensor 43, can be determined according to the following manner.

Assume that generating point S is shifted by Q* so that the pencil beam with tilt angle $\alpha_k$ is parallel shifted by Q*. The cross point of the pencil beam and the linear sensor arrangement is shifted by Qk along the arrangement of sensor 43*. If the linear arrangement of sensor 43 is exactly in parallel to the locus of point S, Qk is equal to Q*, as may be seen from the illustration of FIG. 9. However, as shown by a broken line 43* in FIG. 9, if the linear arrangement of sensor 43 is inclined by $\theta^*$ from the parallel solid line 43, the shift amount Qk of the above pencil beam detected by the sensor elements on broken line 43* becomes smaller by $\Delta$Qk than Q*. When $\theta^*$ is small, such a deviation amount $\Delta$Qk may be represented as:

$$\Delta QK = -Q^* \cdot \tan \theta^* \cdot \tan \alpha_k \qquad (15)$$

The value of $\Delta$Qk may be measured each for $\alpha 1$, $\alpha 2$, $\alpha 3$, $\alpha 4$ and $\alpha 5$ (i.e., k=1, 2, 3, 4 and 5), by sensor 43 on broken line 43*. In this case, tan $\theta^*$ in Eq.(15) may be represented as:

$$\tan \theta^* = -(1/Q^*)(1/5)\,[(\Delta Q1/\tan \alpha 1)w1 + \qquad (16)$$
$$(\Delta Q2/\tan \alpha 2)w2 + \ldots + (\Delta Q5/\tan \alpha 5)w5]$$

where each of $w_k$ (k=1, 2, ..., 5) denotes a given weighting coefficient, provided that $$w_k \propto |\tan \alpha_k| \text{ and } \sum_k w_k = 1.$$

The angle $\theta^*$ of the inclination of radiation sensor 43, which represents the degree of the deviation from the parallel, may be obtained by modifying Eq.(16) as:

$$\theta^* = \tan^{-1}\left\{-(1/5Q^*) \times \left[\sum_k \Delta Qk(|\tan \alpha_k|/\tan \alpha_k)\right] \Big/ \left[\sum_k |\tan \alpha_k|\right]\right\} \qquad (17)$$

Here, tan $\alpha_k$ of Eqs.(16) and (17) for k=1, 2, ..., 5 may be obtained from the following relations:

$$\begin{aligned}
\tan \alpha 1 &= (-lo - 2d1)/l1 \\
\tan \alpha 2 &= (-lo - d1)/l1 \\
\tan \alpha 3 &= -lo/l1 \\
\tan \alpha 4 &= (-lo + d1)/l1 \\
\tan \alpha 5 &= (-lo + 2d1)/l1
\end{aligned} \qquad (18)$$

The calculation of Eqs.(17) and (18) is performed by CPU 51 in FIG. 2.

According to the calculated value of $\theta^*$ of Eq.(17), CPU 51 controls the locus correction driver 29 in FIG. 1, so that of value of $\theta^*$ is automatically minimized.

Figure 9:
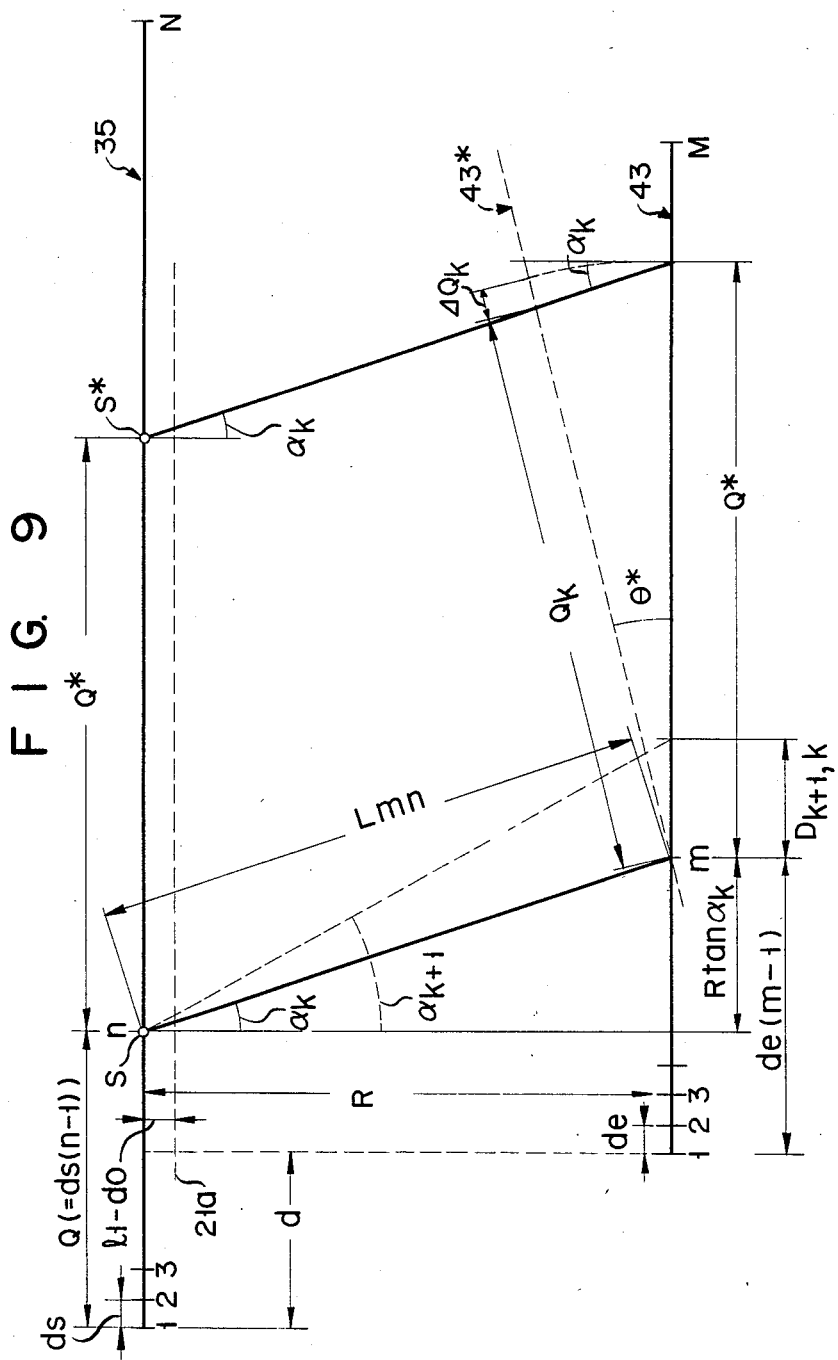
FIG. 9 illustrates the geometrical relationship between the radiation generator (35) and the radiation sensor (43), which is useful to explain how to detect the deviation from the parallel between the locus of the radiation sensing point (S) and the linear arrangement of the radiation sensor (43)

As may be seen from the geometrical relation in FIG. 9, the following holds:

$$D_{k+1,k} = R(\tan \alpha_{k+1} - \tan \alpha_k) \qquad (19)$$

where $D_{k+1,k}$ denotes the distance between an element of sensor 43 for sensing the radiation of tilt angle $\alpha_k$ and another element of sensor 43 for sensing the radiation of tilt angle $\alpha_{k+1}$. Distance R between radiation generator 35 and radiation sensor 43 can be obtained by modifying Eq.(19) as:

$$R = (D_{k+1,k})/(\tan \alpha_{k+1} - \tan \alpha_k) \qquad (20)$$

where k=1, 2, ..., 5.

The following relation can also be derived from FIG. 9:

$$d + de(m-1) - R \tan \alpha_k = Q = ds(n-1) \qquad (21)$$

A horizontal displacement d, which is measured for the tilt angle $\alpha_k$, can be obtained by modifying Eq.(21) as:

$$d = R \tan a_k + ds(n-1) - de(m-1) \quad (22)$$

The horizontal displacement d illustrated in FIGS. 4 and 9 may be obtained as a mean value of $d_k$:

$$d = \sum_k d_k / \sum_k l \quad (23)$$

wherein $d_k$ indicates displacement d for each parameter k.

Further, the following relation can be derived from FIG. 9:

$$Lmn^2 = R^2 + (R \tan a_k)^2 \quad (24)$$

$$R \tan a_k = d + de(m-1) - ds(n-1) \quad (25)$$

The distance Lmn between radiation generating point n and radiation sensing point m may be represented by the following relation, which is obtained from Eqs.(24) and (25):

$$Lmn = \sqrt{R^2 + [d + de(m-1) - ds(n-1)]^2} \quad (26)$$

When object 50 to be inspected partly protrudes beyond a cetain area defined by the radiation of beams 39, such a protrusion will cause an error or inaccuracy in the reconstructed CT image of object 50. This is because such a protrusion causes an artifact in the CT image. In the following, the above protrusion will be discussed with reference to FIGS. 10 to 13.

Figure 10:
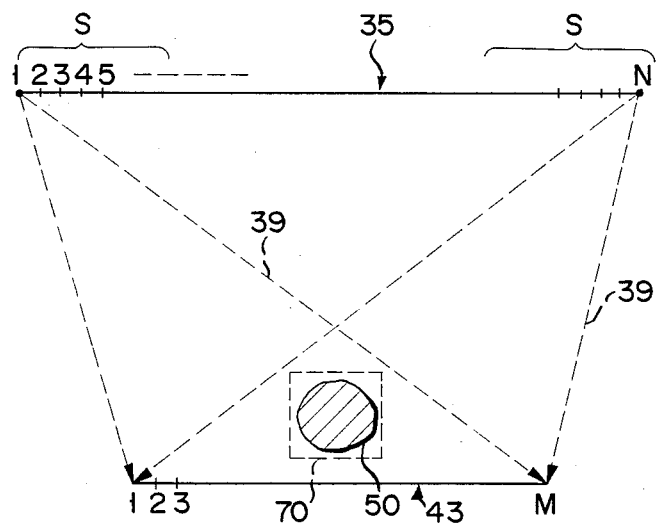
FIG. 10 illustrates how the object to be inspected (50) completely falls within the scanning area of the fan beam (39)
Figure 11:
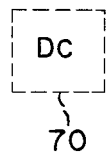
FIG. 11 shows the reconstructing region (70) for effecting the sequential approximation in the case of FIG. 10.

FIG. 10 shows a case where object 50 is completely contained within an area 70 for effecting the image reconstruction, i.e., no protrusion exists. In this case, all of reconstruction area 70 are used as a sequential approximating region Dc, as shown in FIG. 11, and radiation generator 35 and radiation sensor 43 are set around object 50 so that object 50 is completely encompassed by area 70 (region Dc). If the above protrusion exists, an erroneous or inaccurate CT image of object 50 will result.

Figure 12:
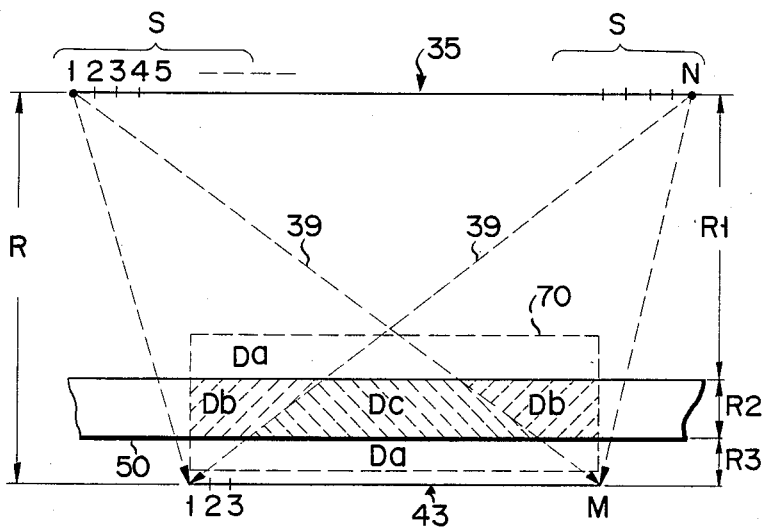
FIG. 12 illustrates how an object (50) partly protrudes beyond the scanning area of the fan beam (39)

FIG. 12 shows a case where image reconstruction area 70 fails to completely encompass object 50, i.e., the protrusion exists. In this case, area 70 may be divided into three regions Da, Db and Dc. In region Da, the value of image data $\mu$ is assumed to be, e.g., zero ($\mu=0$). In region Db, the value of data $\mu$ is assumed to be fixed at $\overline{\mu}$ ($\mu=\overline{\mu}=$constant). In region Dc, the value of data $\mu$ is varied with the sequential approximation. Namely, during the sequential approximating operation, the value of image data $\mu$ of region Dc varies while image data $\mu$ of regions Da and Db are fixed.

In the above case, radiation generator 35 and radiation sensor 43 are set around object 50 so that object 50 matches with the boundary between regions Da and Dc and with that between regions Da and Db. The data of a distance R1 between generator 35 and object 50, and the data of a distance R3 between sensor 43 and object 50, are obtained by actual measurement. The data of distance R can be obtained from the calculation of Eq.(20). The data of distance R2 may be obtained from the data of R, R1 and R3. According to the data of R and R1–R3, and to the angle data of beams 39, CPU 51 calculates the boundary between regions Db and Dc. (The above beam angle data represents each inclination of the intermediate two broken lines of beams 39 shown in FIG. 12.) Then, the boundaries among regions Da, Db and Dc within reconstruction area 70 are patterned in CPU 51, as shown in FIG. 13.

Figure 13:
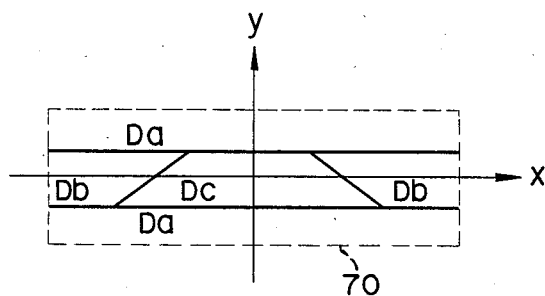
FIG. 13 shows the reconstructing region (70) for effecting the sequential approximation in the case of FIG. 12.

After completing the patterning of regions Da, Db and Dc as shown in FIG. 13, CPU 51 calculates the value of image data $\overline{\mu}$, using the aforementioned preprocessed data $\tau m(m,n)$, according to the following relation:

$$\overline{\mu} = \overline{\tau m(m,n)} / \overline{tmn} \quad (27)$$

wherein tmn denotes the length of the radiation path of beam 39 passing through regions Db. Incidentally, the calculation of Eq.(27) may be performed only for certain radiation paths of beams 39 selected at intervals, thereby simplifying the calculation of Eq.(27).

In general, the value $\overline{\mu}$ of image data $\mu$ of region Db is not constant for an actual inspection object. Consequently, the assumption of "$\mu=\overline{\mu}=$constant" will cause an artifact in the reconstructed CT image of the object. However, when region Db contains no particular portion whose X-ray absorption coefficient is prominently different from the portion therearound, variations in image data value $\overline{\mu}$ of region Db do not substantially spoil the quality of the reconstructed CT image for region Dc. Further, even if region Db contains a strange portion having a prominently different X-ray absorption coefficient, an artifact caused by such a strange portion appears only near the boundary between regions Db and Dc. Therefore, regardless of variations in value $\overline{\mu}$ of region Db, a practical and useful CT image of an actual object can be obtained.

If the boundary data of regions Da, Db and Dc is available for an inspection with said protrusion, a useful CT image can be obtained for any object having a figure other than a wall-like figure. In any case, the accuracy of the obtained CT image depends on the preciseness of data of regions Da, Db and Dc used in the reconstructing operation. According to the above-mentioned embodiment of the present invention, since radiation generator system 20 is separated from and independent of radiation sensor system 40, a CT image of an immovable onject (50) to be inspected, e.g., a leg of a bridge, can be obtained by properly setting the radiation generator/sensor systems 20 and 40 around the object. In this case, leveling instruments 33 and 45 crossing at right angles and provided for systems 20 and 40, respectively serve to simplify the adjustment to make the radiation plane of beams 39 from system 20 passing through the linear sensor arrangement of system 40.

Further, according to the embodiment, collimator plate 37 with multi-slits is movably located in front of radiation generator 35, while radiation generator system 20 is made rotatable around its end portion. From this, the distance (R) between systems 20 and 40 can be calculated using pencil beams obtained by collimator plate 37, while the parallel adjustment between systems 20 and 40 can be achieved by controlling the rotation of system 20 according to the calculated result ($\theta^*$) of the inclination of radiation sensor 43 with respect to the scanning locus of radiation generating point S.

In addition, even if object 50 (e.g., a long and high wall) protrudes beyond the sequential approximating region Dc, when image data fixed regions Da and Db and image data variable region Dc are provisionally known with respect to reconstruction area 70, a practical and useful CT image of object 50 can be obtained according to the embodiment of the invention.

The present invention should not be limited to the above embodiment. Various changes or modifications may be made without departing from the scope of the invention as claimed.

Figure 14:
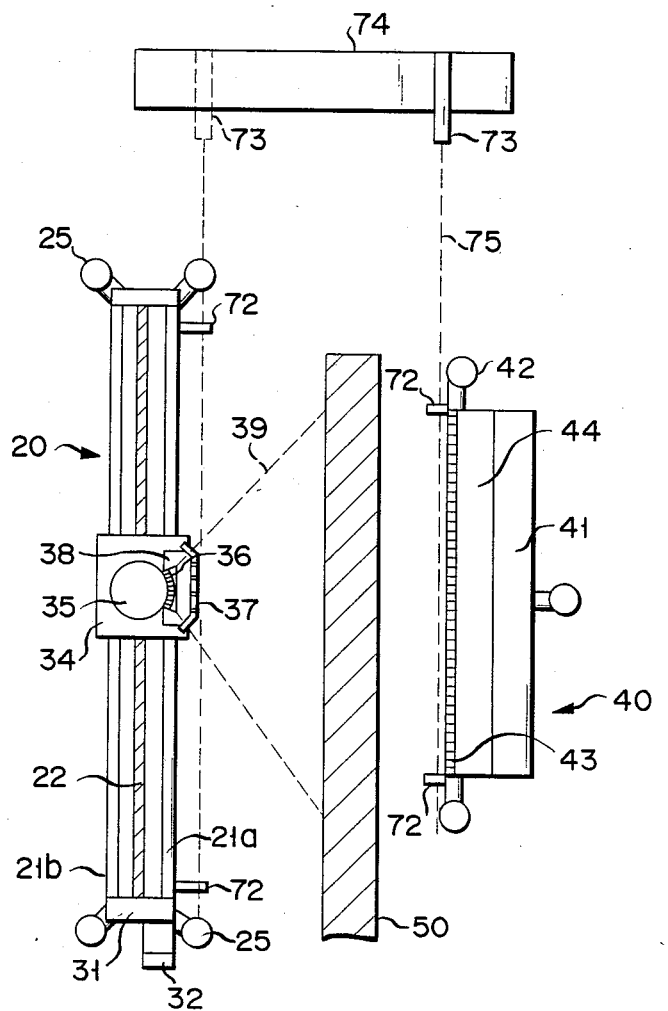
FIG. 14 shows another embodiment of a tomographic apparatus according to the present invention.

FIG. 14 shows another embodiment of a tomographic apparatus according to the present invention. In the FIG. 14 apparatus, leveling instruments 33, 45 and locus correction driver 29 used in the embodiment of FIG. 1 are not employed but, instead, laser light is utilized for positioning between radiation generator/sensor systems 20 and 40. Further, in the FIG. 14 apparatus, positioning indicators 72 are provided at both side portions of each of systems 20 and 40. Each of these indicators 72 may have a configuration as shown in FIG. 15A. Thus, indicator 72 is formed with a glass plate 72a on which a cross index 72b is marked at its center.

The FIG. 14 apparatus is further provided with a laser light device 74 on which a laser oscillator 73 is mounted, as shown in FIG. 15B. Device 74 is formed of a horizontal guide body 74a, a vertical guide body 74b, a horizontal distance meter 74c and a vertical distance meter 74d. Vertical guide body 74b is vertically and movably set on horizontal guide body 74a. The horizontal shift amount of body 74b is measured by horizontal distance meter 74c attached to body 74b. The vertical shift amount of laser oscillator 73 mounted on body 74b is measured by vertical distance meter 74d attached to oscillator 73. The vertical and horizontal locations of a laser beam 75 delivered from oscillator 73 can be determined from the measurement of meters 74c and 74d.

When object 50 has a lengthened figure as shown in FIG. 14, laser light device 74 is set at one side of object 50, such that the locus of the horizontal shift of laser beam 75, along guide body 74a, crosses perpendicularly to the longitudinal direction of object 50. In other words, device 74 is set so that laser beam 75 is substantially parallel to the longitudinal direction of object 50.

After the above setting of laser light device 74, laser oscillator 73 is located at the right side of FIG. 14, so that laser beam 75 passes through each cross index 72b of two positioning indicators 72 provided at both sides of sensor system 40. If beam 73 does not simultaneously pass through both indexes 72b of two indicators 72, the body of system 40 is slightly moved so that beam 75 passes through both indexes 72b, simultaneously. Then, laser oscillator 73 is shifted to the left side of FIG. 14, so that beam 75 from laser oscillator 73 passes through each cross index 72b of two positioning indicators 72 provided at both sides of generator system 20. If beam 75 does not simultaneously pass through both indexes 72b, the body of system 20 is moved so that beam 75 passes through both indexes 72b, simultaneously.

After completing the above adjustment of systems 20 and 40 using the laser beam, system 20 is exactly parallel to system 40. Further, the distance between systems 20 and 40 can be determined from the measurement of horizontal distance meter 74c as shown in FIG. 15B.

Incidentally, if two laser oscillators 73 are provided on body 74a in parallel, spaced apart for a prescribed distance, no horizontal shifting of laser oscillator 73 is necessary.

FIG. 16 shows still another embodiment of a tomographic apparatus of the invention. In the FIG. 16 apparatus, generator and sensor systems 20 and 40 are provided with swing arm mechanisms 80 and 81, respectively. Further, generator system 20 is formed of an electrically scanning radiation generator 35*, which may be a conventional one. Generator 35* is supported by one end of arm mechanism 80, the other end thereof being held by an arm support 85 mounted on a generator table 83. The four corners of table 83 are provided with fixing pads 82. Then, table 83 having generator 35* is fixed on a floor or ground via pads 82. Similarly, an assembly of radiation sensor 43 and data collector 44 is supported by one end of arm mechanism 81, the other end thereof being held by an arm support 86 mounted on a sensor table 84. The four corners of table 84 are provided with fixing pads, though which table 84 having the sensor/collector assembly (43,44) is fixed on the floor or ground.

As shown in FIG. 16, a certain portion of object 50 is inserted between sensor 43 and generator 35*. Arm mechanisms 80 and 81 are adjusted such that sensor 43 faces the radiation output portion of generator 35* via object 50 and, at the same time, sensor 43 is parallel to generator 35*. The method for detecting the deviation from the parallel of sensor 43 and generator 35* may be the same as has already been described with reference to FIG. 9.

The sensor/collector assembly (43,44) is coupled via a signal cable 84a to a data processor 87. Also, generator 35* is coupled via a signal cable 83a to processor 87. Processor 87 may have a configuration as shown in FIG. 2. After completing the parallel adjustment between sensor 43 and generator 35*, processor 87 renders the generator 35* active, so that suitable X-ray radiations are delivered from generator 35*. Then, respective sensor elements of sensor 43 catch X-ray radiations passing through object 50. The data of these radiations are collected by data collector 44, and the collected data is sent to processor 87. Thereafter, the CT image of object 50 is reconstructed by the operation of processor 87.

According to the embodiment of FIG. 16, the flexibility with respect to the setting manner of the tomographic apparatus is better than that of the embodiment of FIG. 1.

Incidentally, radiation generator 35* may be provided with a reference detector (36) in front thereof, as in the case of the FIG. 1 embodiment.

Figure 17:
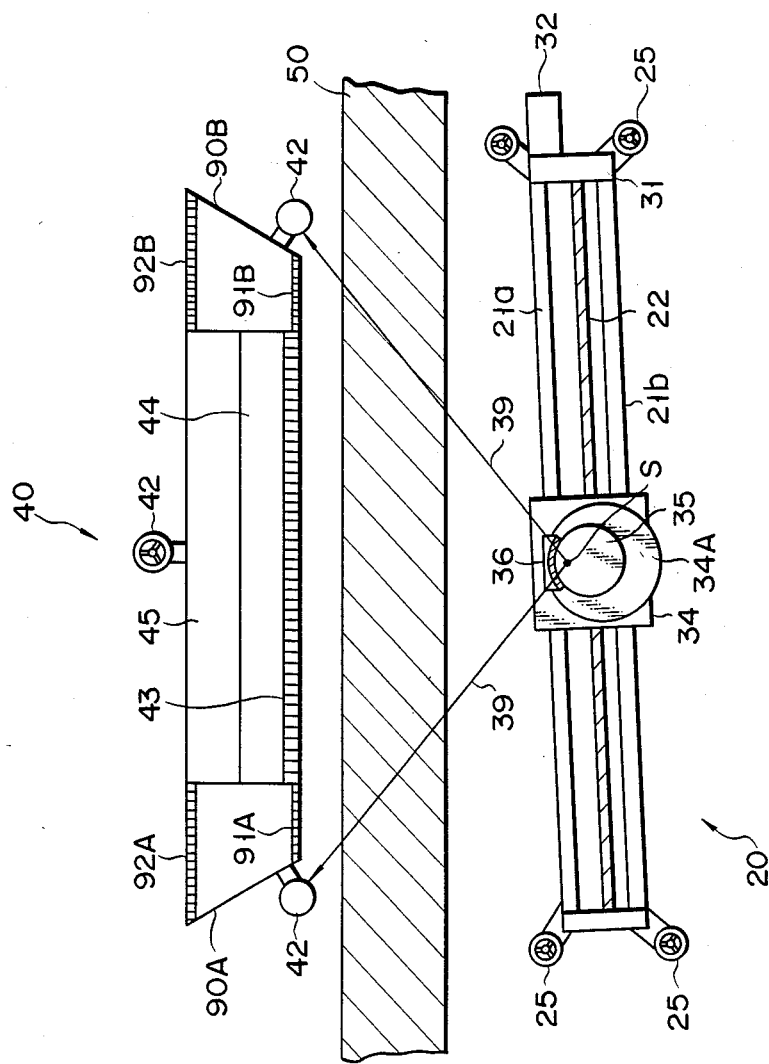
FIG. 17 shows an upper-side view of the mechanical part of a tomographic apparatus according to another embodiment of the present invention.

FIG. 17 shows an upper-side view of the mechanical part of a tomographic apparatus according to another embodiment of the invention, wherein radiation generator system 20 is slightly inclined with respect to radiation sensor system 40, i.e., systems 20 and 40 are not in parallel to each other. The FIG. 17 embodiment is characterized by the use of radiation sensor devices 90A and 90B respectively comprising collimator plates 91A, 91B and two-dimensional radiation sensors 92A, 92B. One sensor device 90A, associated with collimator plate 91A and two-dimensional sensor 92A, is located at the left side of radiation sensor system 40, as shown in FIG. 17. On the other hand, the other sensor device 90B, associated with collimator plate 91B and two-dimensional sensor 92B, is located at the right side of system 40.

Figure 19A:
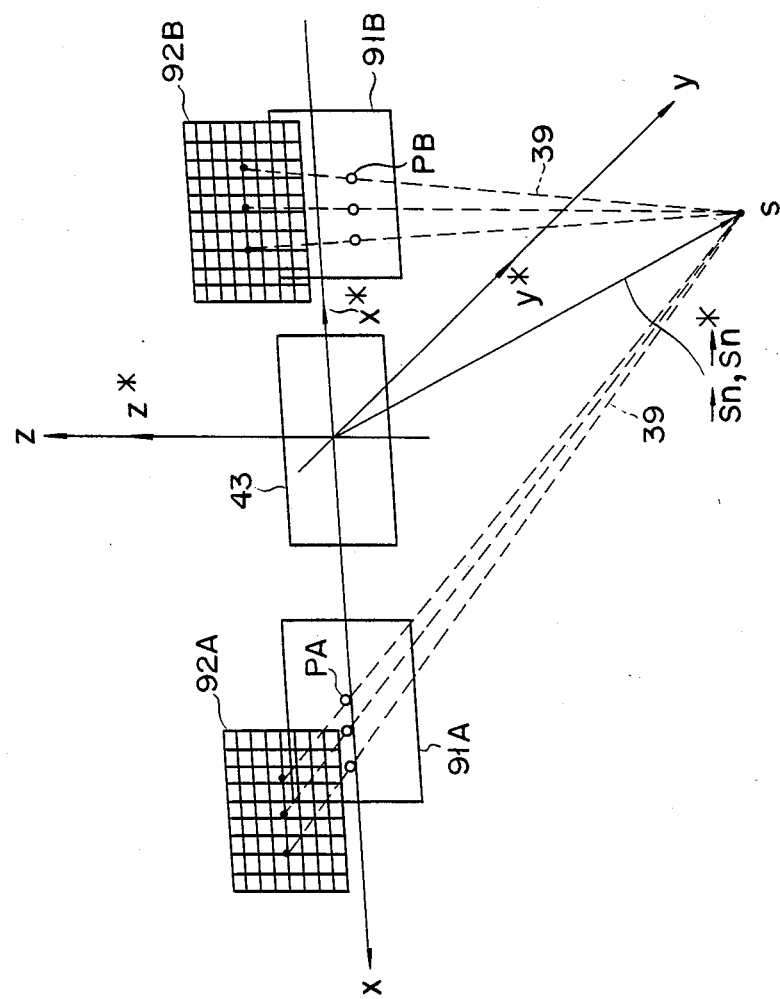
FIG. 19A shows the geometrical relationship between the radiation generating point (S) and each of the radiation sensing points of two-dimensional radiation sensors (92, 92B) of FIG. 17.

Collimator plates 91A and 91B are provided with pinholes PA and PB, respectively, through which radiation beams 39 are transmitted (see FIG. 19A). The pinhole beams passing through collimator plates 91A and 91B are sensed by two-dimensional radiation sensors 92A and 92B. Also, radiation generator 35 of the FIG. 17 embodiment is mounted on scanner frame 34 via a swing (or rotor) mechanism 34A. By means of swing mechanism 34A, the radiating direction of beams 39 from radiation 35 can be changed so that the scanning area of beams 39 completely covers radiation sensors 92A, 92B and 43.

FIG. 18 shows a block configuration of the electrical part of the FIG. 17 embodiment. As shown in FIG. 18, X-ray absorption data delivered from sensors 90A and 90B are supplied via data collector 44 to CPU 51. Other configurations of FIG. 18 may be the same as those shown in FIG. 2. (The same reference numerals used in FIGS. 2 and 18 denote the same circuit elements.)

Figure 19B:
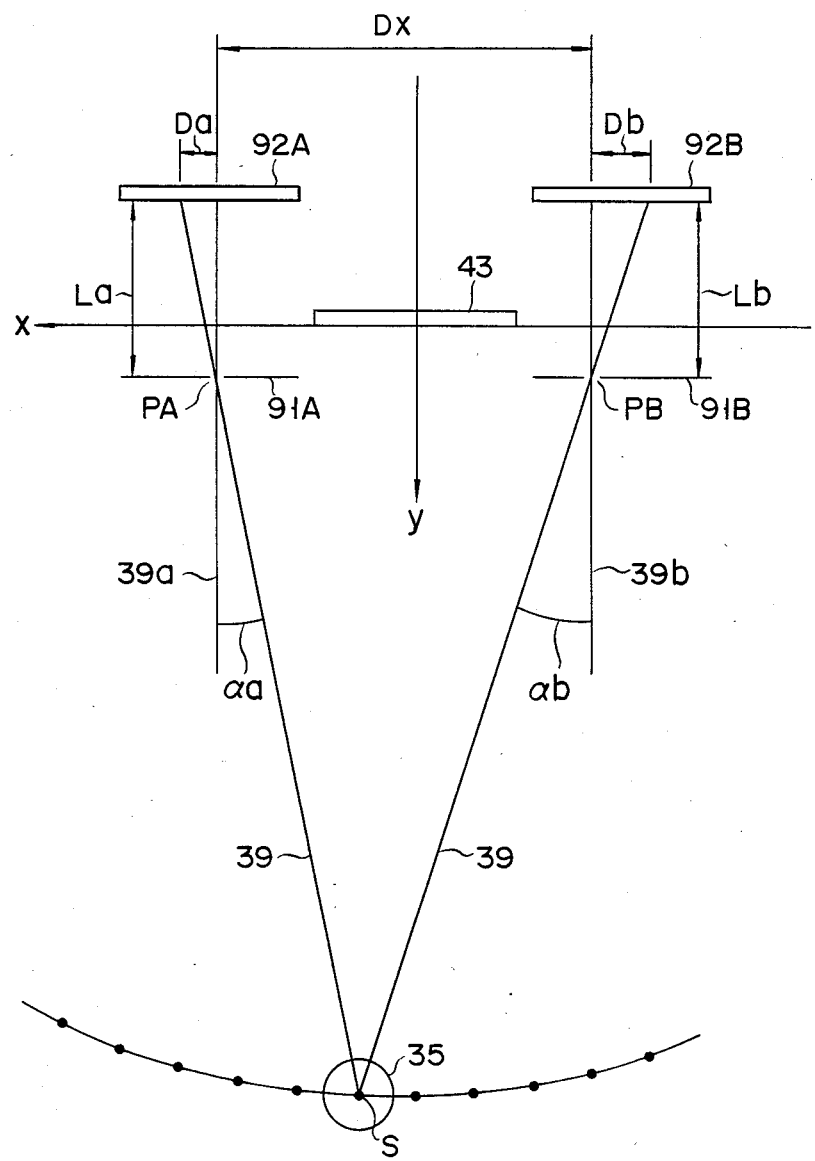
FIG. 19B, shows a x-y plane view of the geometrical relationship of FIG. 19A.
Figure 20:
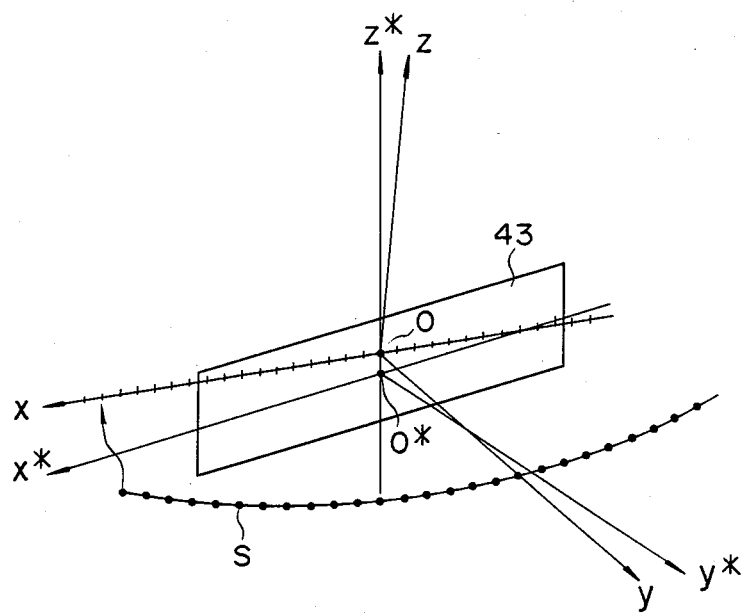
FIG. 20 shows the geometrical relationship between the radiation generating point (S) and the radiation sensor (43) of FIG. 17.

FIGS. 19A and 19B show the geometrical relationship between the radiation generating point S and each of the radiation sensing points of two-dimensional radiation sensors 92A and 92B. Also, FIG. 20 shows the geometrical relationship between the radiation generating point S and the radiation sensor 43. In FIGS. 19A and 20, the coordinate system $(x^*,y^*,z^*)$ is defined as a reference of sensors 92A, 92B and 43, and the coordinate system $(x,y,z)$ is defined as a reference of the locus of radiation generating point S. The plane of the sensor elements in sensor 43 is on the $x^*$-$z^*$ plane of $(x^*,y^*,z^*)$ coordinate system. The radiation plane (hereinafter referred to as a slice plane) of beams 39 is on the x-y plane of $(x,y,z)$ coordinate system. The x axis of $(x,y,z)$ coordinate system is on the cross-line between the $x^*$-$z^*$ plane and the slice plane. Further, as shown in FIG. 20, the origin O of $(x,y,z)$ coordinate system is on the $z^*$ axis of $(x^*,y^*,z^*)$ coordinate system. The locus of radiation sensing point is on the x axis of $(x,y,z)$ coordinate system.

The position of radiation generator point S with respect to $(x^*,y^*,z^*)$ coordinate system may be represented as $\vec{Sn}^*(Snx^*, Sny^*, Snz^*)$, while the position of point S with respect to $(x,y,z)$ coordinate system may be represented as $\vec{Sn}(Snx, Sny, O)$. (The z axis component of $\vec{Sn}$ is 0.) Meanwhile, the radiation sensing point of sensor 43 with respect to $(x^*,y^*,z^*)$ coordinate system may be represented as $\vec{Dm}^*(Dmx^*,0,Dmz^*)$, and the sensing point of sensor 43 with respect to $(x,y,z)$ coordinate system may be represented as $\vec{Dm}(Dmx,0,0)$. (The $y^*$ axis component of $\vec{Dm}^*$, and the y and z axes components of $\vec{Dm}$, are 0.)

In the following, how the position of radiation generating point S with the inclined locus is detected will be explained.

When the height of the locus of point S is the same as that of the sensor element arrangement of sensor 43 and the locus of point S is parallel to the arrangement of sensor 43, the system of $(x,y,z)$ coordinate is identical to the system of $(x^*,y^*,z^*)$ coordinate. In this case, radiation beams 39 from generator 35 pass through respective pinholes PA and PB, and the pinhole beams passing through pinholes PA and PB are sensed by two-dimensional radiation sensors 92A and 92B.

The distance La between collimator plate 91A and sensor 92A, and the distance Lb between collimator plate 91B and sensor 92B, as shown in FIG. 19B, are known data. Further, the position of pinhole beam 39a, which passes through pinhole PA perpendicularly to the plane of collimator plate 91A, can be determined from the data of the above pinhole beam 39a sensed by sensor 92A, according to a prescribed operation of CPU 51. Similarly, the position of pinhole beam 39b perpendicularly passing through pinhole PB of collimator plate 91B can be determined from the data of the pinhole beam 39b sensed by sensor 92B according to the operation of CPU 51.

In the main scanning of the radiation, beams 39 generated from point S and projected onto two-dimensional sensors 92A and 92B, respectively via pinholes PA and PB of collimator plates 91A and 91B, are sensed by certain sensor elements of sensors 92A and 92B. Then, the pinhole beam position data thus obtained from sensors 92A and 92B are supplied via data collector 44 to CPU 51. In CPU 51, deviations (e.g., Da and Db in FIG. 19B) of the above pinhole beam position data with respect to the x, y and z directions are calculated, based on the aforementioned known position data of pinhole beams 39a and 39b perpendicularly passing through pinholes PA and PB.

As will be seen from FIG. 19B, the inclination ($\alpha a$) of beam 39 with respect to the plane of collimator plate 91A can be calculated ($\alpha a = \tan^{-1}(Da/La)$) from the data (La) of said distance between plate 91A and sensor 92A, and from the data (Da) of said deviation of the pinhole beam position obtained from sensor 92A in the main scan. Similarly, the inclination ($\alpha b$) of beam 39 with respect to the plane of collimator plate 91B can be calculated ($\alpha b = \tan^{-1}(Db/Lb)$) from the data (Lb) of said distance between plate 91B and sensor 92B, and from the data (Db) of said deviation of the pinhole beam position obtained from sensor 92B in the main scan.

The distance between pinholes PA and PB is known data (Dx). According to data Dx, Da, Db, $\alpha a$ and $\alpha b$, the position of radiation generating point S, which appears at the cross-point of beams 39, can be known by a conventional geometrical calculation performed in CPU 51. Then, the position $\vec{Sn}^*(Snx^*, Sny^*, Snz^*)$ of point S defined by the $(x^*,y^*,z^*)$ coordinate system is determined, and the slice plane of fan beams 39 containing point S is obtained.

The $(x,y,z)$ coordinate system is determined according to the slice plane, so that the slice plane is on the x-y plane of the $(x,y,z)$ system. When the coordinate systems of $(x,y,z)$ and $(x^*,y^*,z^*)$ are determined, the conversion coefficient T between these coordinate systems is determined. Then, the position $\vec{Sn}(Snx,Sny,0)$ of point S is obtained by the calculation of $\vec{Sn} = T \cdot \vec{Sn}^*$.

Radiation sensing point $\vec{Dm}(Dmx,0,0)$ of sensor 43 with respect to $(x,y,z)$ coordinate system, which is not necessarily identical to the position of the sensor element in sensor 43, is defined on the x axis of $(x,y,z)$ system. Then, sensing point $\vec{Dm}^*(Dmx^*,0,Dmz^*)$ with respect to $(x^*,y^*,z^*)$ coordinate system is calculated from the data of $\vec{Dm}(Dmx,0,0)$ and conversion coefficient T ($\vec{Dm}^* = T^{-1} \cdot \vec{Dm}$).

Figure 21:
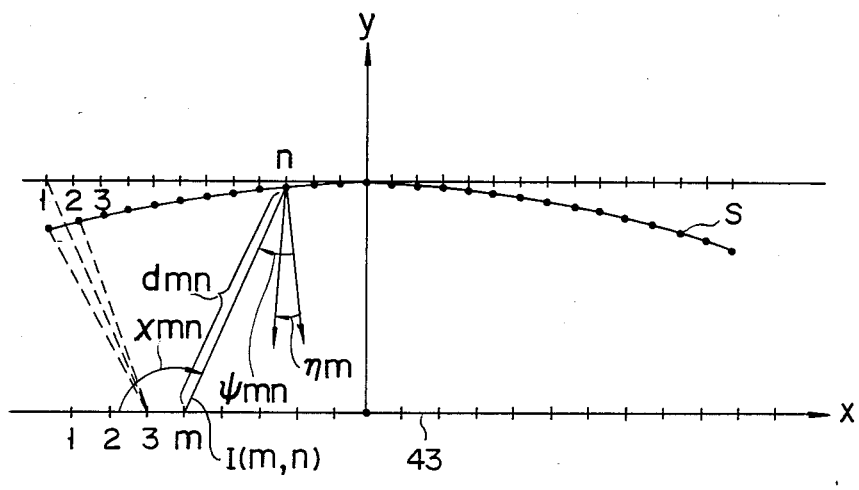
FIG. 21 shows another geometrical relationship between the radiation generating point (S) and the radiation sensor (43), with respect to the x-y plane of the (x,y,z) coordinate system in FIG. 20.

FIG. 21 shows the geometrical relationship between the locus of radiation generating point S and the sensor element array of sensor 43 located on the x axis of $(x,y,z)$ coordinate system. Data dmn, $\chi$mn, $\Psi$mn and $\eta$m shown in FIG. 21, which are defined with respect to radiation beam path I(m,n), are calculated according to the above $\vec{Dm}$ and $\vec{Sn}$. Data dmn denotes the distance between the nth position of point S and the mth element of sensor 43. Data $\chi$mn denotes the radiation angle of path I(m,n) with respect to the x axis. Data $\eta$m denotes a prefixed angle with respect to the y axis, which is known from the degree of rotation of swing mechanism 34A shown in FIG. 17. X-ray absorption data Iomn, obtained when no inspection object exists, is calculated according to dmn, $\chi$mn, $\Psi$mn and $\eta$m. This calculation is performed utilizing a data table which contains the information of a radiation intensity distribution with respect to the radiating direction of the beam, and the information of a sensitivity change of each sensor element of sensor 43 with respect to the projected beam angle. The above X-ray absorption data Iomn is log-converted into the corresponding data $\tau(m,n)$ according to a log conversion table stored in the memory of CPU 51 in FIG. 18:

$$\tau m(m,n) = \ln(Iomn/Imn) \qquad (28)$$

wherein Imn denotes X-ray absorption data obtained when an inspection object exists.

The radiation sensing point $\vec{Dm}*(Dmx*,0,Dmz*)$ of sensor 43 often deviates from the center of each sensor element of sensor 43. From this, data $\tau m(m,n)*$ used for the actual reconstruction operation of the CT image is obtained by properly interpolating the data of $\vec{Dm}*$.

Figure 22:
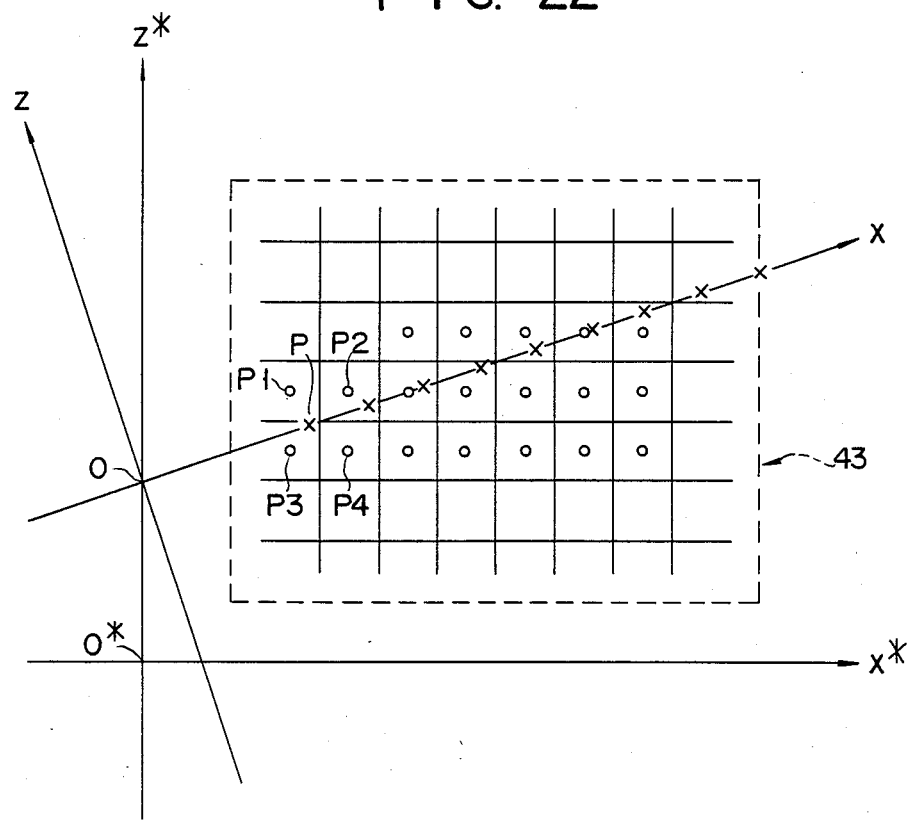
FIG. 22 illustrates an example of the deviation between the center (P1-P4) of each sensor element and the sensing point (P)
Figure 23:
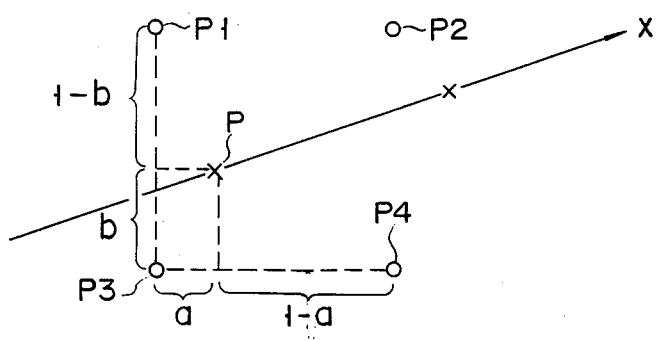
FIG. 23 explains how the sensing point (P) is obtained by an interpolation using the data of sensor elements (P1, P3, P4) in FIG. 22.

FIG. 22 illustrates an example of the above deviation between the center (P1-P4) of each sensor element of sensor 43 and the sensing point (P) of $\vec{Dm}*$. FIG. 23 explains how the sensing point P is obtained by interpolation using the data of sensor elements P1, P3 and P4 shown in FIG. 22.

Radiation sensing point $\vec{Dm}*(Dmx*,0,Dmz*)$ may be represented as $(Dox*+m\Delta Dx*,0,Doz*+m\Delta Dz*)$ in the $x*$-$y*$ plane, while radiation sensing point $\vec{Dm}(Dmx,0,0)$ may be represented as $(Dox+m\Delta Dx,0,0)$ in the x-y plane. Specific four sensor elements P1 to P4, being close to sensing point P, are used to obtain the data of point P, by interpolating the outputs from sensor elements P1 to P4. Each of these outputs from sensor elements P1 to P4 is subjected to offset correction, sensitivity correction, radiation intensity change compensation, and log conversion. Then, the interpolated data $\tau m*(m,n)$ of point P is obtained by the calculation of the relation:

$$\tau m*(m,n) = b[(1-a)\cdot P1 + a\cdot P2] + (1-b)[(1-a)\cdot P3 + a\cdot P4] \qquad (29)$$

After completing the above interpolation calculation, the preprocessed data $\tau m*(m,n)$ obtained for point S with a curved locus is converted to data $\tau m(m,n)$ for point S with a linear locus. Thereafter, the reconstructing operation as has been explained with reference to FIGS. 1 to 13 is performed.

According to the above embodiment, since the exact locus of radiation generating point S is actually obtained by calculation, even if the locus of S deviates from a prescribed linear or circular line, an accurate CT image can be obtained.

Figure 24A:
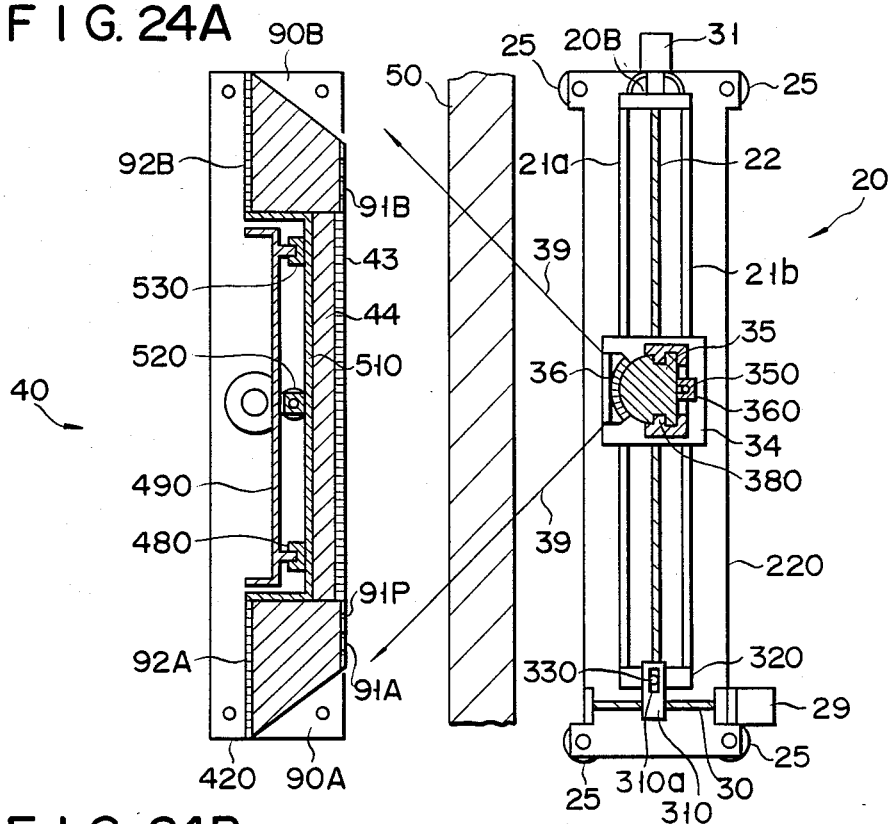
FIG. 24A illustrates an upper-side view of the mechanical part of a tomographic apparatus according to another embodiment of the invention.
Figure 24B:
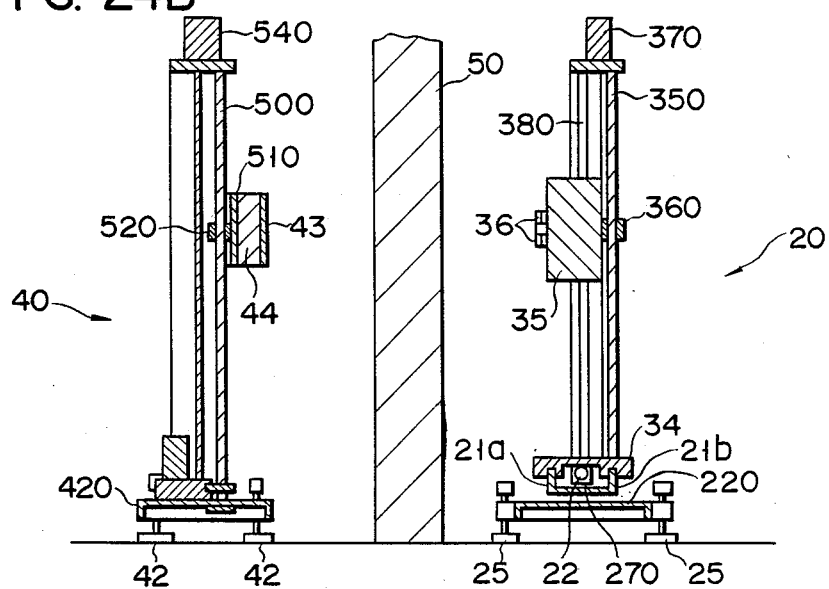
FIG. 24B illustrates a side view of the mechanical part shown in FIG. 24A.

FIG. 24A illustrates an upper-side view of the mechanical part of a tomographic apparatus according to another embodiment of the invention. This embodiment may be regarded as a modification of the FIG. 17 embodiment. FIG. 24B illustrates a side view of the mechanical part shown in FIG. 24A. (The common elements throughout FIGS. 1 to 24 are denoted by the same reference symbols for the sake of simplicity.)

As shown in FIGS. 24A and 24B, scanner frame 34 of apparatus radiation system 20 is mounted on a base member 220. Member 220 is fixed on a floor via fixing pads 25. A guide member 380 stands on frame 34. A lifting screw 350 also stands on frame 34. A tapped piece 360 is fixed at the rear side of radiation generator 35. Screw 350 is screwed through the tapping hole of piece 360. Generator 35 is movably held by guide member 380. The height of radiation 35 with respect to the floor is changed by the clockwise or counterclockwise rotation of screw 350. The rotation force of screw 350 is derived from a lift driver 370.

The above assembly of radiation generator 35 is movable set on guide rails 21a and 21b. A tapped piece 270 is fixed at the bottom of scanner frame 34. Screw 22 is screwed through the tapping hole of piece 270. The radiation generator assembly is moved by the rotation of drive screw 22.

One end portion of rails 21a and 21b, and one end of screw 22, are held at a rotor support mechanism 20B. Scan driver 31 is mounted on mechanism 20B. The rotation force of screw 22 is derived from driver 31. The other end portion of rails 21a and 21b, and the other end of screw 22, are held at a support member 320. Member 320 is provided with a pin 330. Pin 330 is inserted into a rectangular opening 310a of a coupling piece 310, so that member 320 is loosely coupled to piece 310. Piece 310 is engaged with drive screw 30. Screw 30 is rotated by locus correction driver 29. Piece 310 is shifted by the rotation of screw 30, so that one end portion of rails 21a and 21b slightly rotates around rotor support mechanism 20B via the loose coupling between member 320 and piece 310.

Radiation sensor system 40 is assembled on a base member 420. Member 420 is fixed on the floor via fixing pads 42. A guide member 490 stands on member 420. A lifting screw 500 also stands on member 420. A tapped piece 520 is fixed at the rear side of a lifter frame 510. The assembly of radiation sensor 43, data collector 44 and radiation sensor devices 90A, 90B is mounted on lifter frame 510. Screw 500 is screwed through the tapping hole of piece 520. Frame 510 is movably held by guide member 490 at respective pairs of guide rails 480 and guide pieces 530. The height of sensor 43 with respect to the floor is changed by the clockwise or counterclockwise rotation of screw 500. The rotation force of screw 500 is derived from a lift driver 540. Each of collimator plates 91A and 91B has plural pinholes 91P. (Pinholes 91P correspond to pinholes PA and PB shown in FIG. 19A. Although pinholes are used for the pattern of collimator plates 91A and 91B, other pattern may be used, of course.)

The electrical part to be adapted to the mechanical part of FIGS. 24A and 24B may be the same as shown in FIG. 18. The circuit operation of the electrical part adapted to the FIGS. 24A and 24B embodiment may be the same as that of the FIG. 17 embodiment.

According to the FIGS. 24A and 24B embodiment, even if the locus of radiation generating point S is not exactly linear or circular, an accurate CT image can be obtained. This is because the exact locus of radiation generating point S is actually calculated for each CT inspection.

Figure 25:
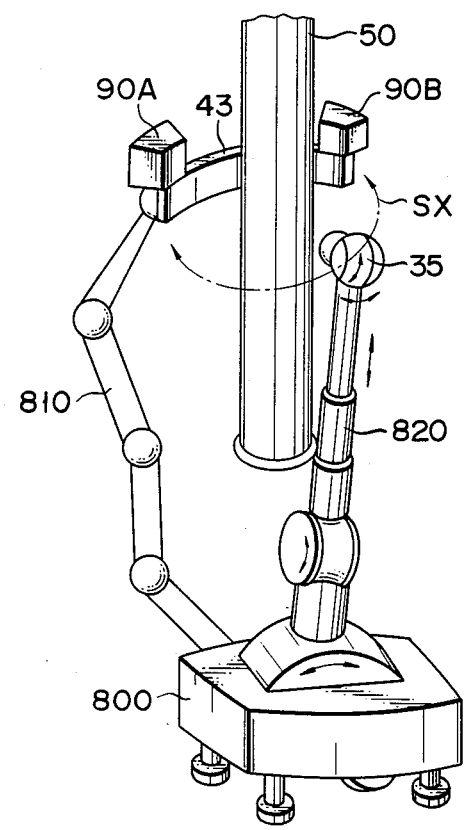
FIG. 25 is a perspective view of a tomographic apparatus according to another embodiment of the invention.

FIG. 25 is a perspective view of a tomographic apparatus according to another embodiment of the invention. This embodiment may be regarded as a modification of the FIG. 16 embodiment. According to the FIG. 25 embodiment, the electrical part as shown in FIG. 18 is contained in a main frame 800. Radiation generator 35 is supported by the top end portion of a multi-joint flexible arm 820. The bottom end portion of arm 820 is fixed at main frame 800. By means of flexible arm 820, the locus (SX) of radiation generating point S of generator 35 can be made circular.

A curved radiation sensor 43 with sensor devices 90A and 90B is supported by the top end portion of a multi-joint flexible arm 810. The bottom end portion of arm 810 is fixed at main frame 800. By means of flexible arms 810 and 820, object 50 can be set roughly at the center of the circle defined by the curved arrangement of sensor 43 and the circular locus SX of generator 35.

Although the circular locus SX often deviates from an exact circle, such a locus deviation can be compensated for by calculating the position of point S according to a manner as described with reference to FIGS. 19 to 23.

Figure 26A:
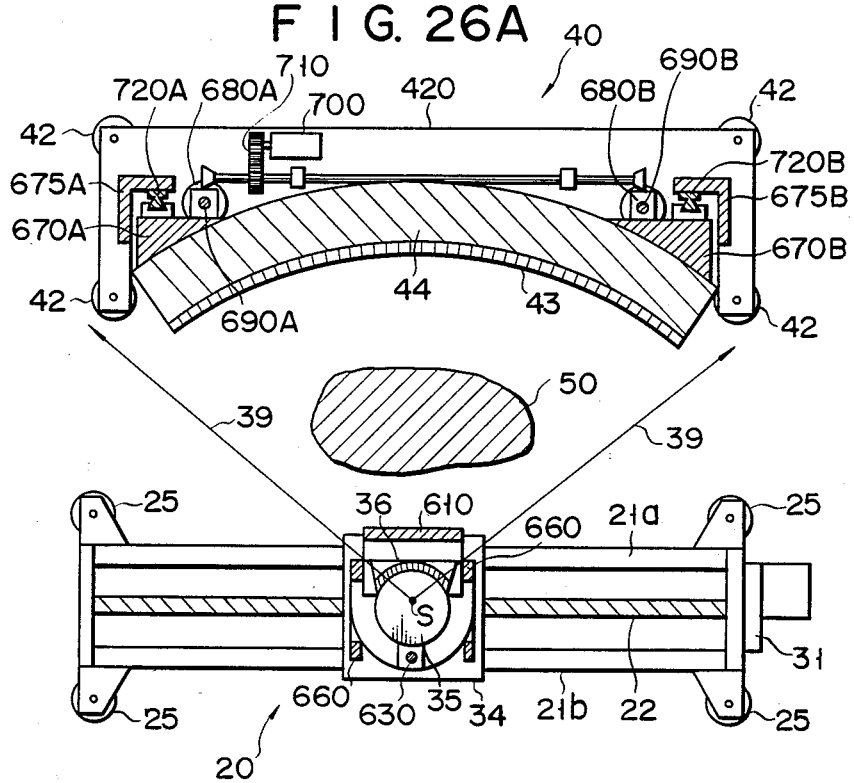
FIG. 26A illustrates an upper-side view of the mechanical part of a tomographic apparatus according to another embodiment of the invention.
Figure 26B:
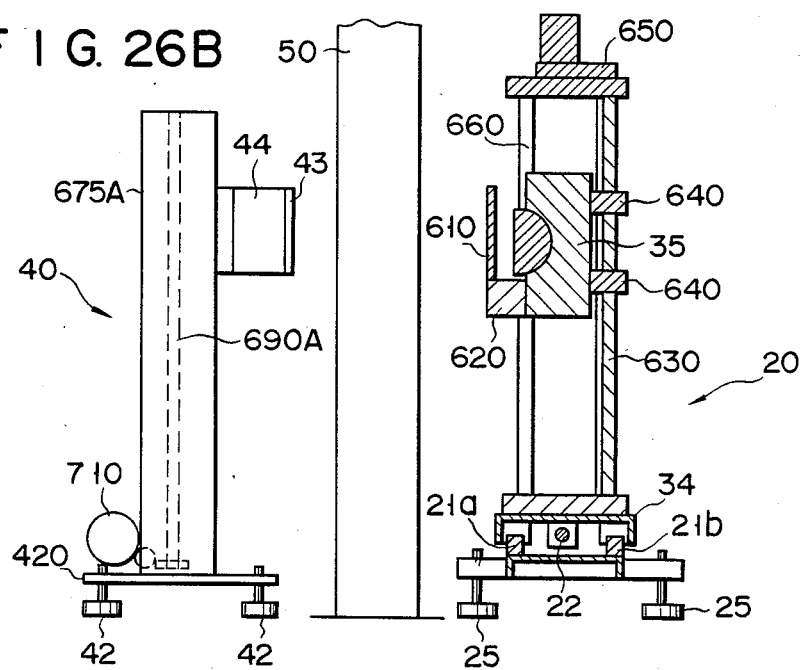
FIG. 26B illustrates a side view of the mechanical part shown in FIG. 26A.

FIG. 26A illustrates an upper-side view of the mechanical part of a tomographic apparatus according to another embodiment of the invention. This embodiment may be regarded as a modification of the FIGS. 24A and 24B embodiment. FIG. 26B illustrates a side view of the mechanical part shown in FIG. 26A. The electrical part as shown in FIG. 2 may be adapted to the mechanical part of FIGS. 26A and 26B. The circuit operation of the electrical part adapted to the FIGS. 26A and 26B embodiment may be the same as that of the FIG. 2 embodiment. (The common elements among FIGS. 24A, 24B and 26A, 26B are denoted by the same reference symbols for the sake of simplicity.)

As shown in FIGS. 26A and 26B, scanner frame 34 of radiation generator system 20 is movably mounted on the assembly of guide rails 21a and 21b. The guide rail assembly is fixed on a floor via fixing pads 25. A guide member 660 stands on frame 34. A lifting screw 630 also stands on frame 34. Tapped pieces 640 are fixed at the rear side of radiation generator 35. Screw 630 is screw through the tapping hole of each of pieces 640. Generator 35 is movably held by guide member 660. The height of generator 35 with respect to the floor is changed by the clockwise or counterclockwise rotation of screw 630. The rotation force of screw 630 is derived from a lift driver 650.

Radiation generator 35 is provided with a multi-pinhole shutter 610 and a shutter driver 620. Before starting the main CT scanning, shutter 610 is closed by driver 620 while the scanning of radiations from generator 35 is performed. In this case, multi-pencil beams are supplied from generator 35 to sensor 43. Radiation absorption data obtained by this scanning is supplied to CPU 51 (FIG. 2, etc.). Data (lo, dl, $a_k$ in FIG. 8) of the location of the pinholes of shutter 610 and the data (l1) of the distance between each pinhole and point S, are precedently supplied to CPU 51, as has been described with reference to FIG. 8. CPU 51 determines each radiation generating point S in accordance with the above precedently supplied data, using a known trigonometry. The data of point S thus determined is stored in the memory of CPU 51, and the stored data is utilized in the main CT scanning. In the main CT scanning, shutter 610 is opened by driver 620, so that fan beam 39 (not a pencil beam) is radiated toward object 50.

Radiation sensor system 40 is assembled on a base member 420. Member 420 is fixed on the floor via fixing pads 42. Guide members 675A and 675B stand on member 420. Lifting screws 690A and 690B also stand on member 420. Tapped pieces 680A and 680B are fixed at the respective rear sides of support blocks 670A and 670B. The assembly of radiation sensor 43 and data collector 44 is supported by blocks 670A and 670B. Screws 690A and 690B are screwed through the respective tapping holes of pieces 680A and 680B. Support blocks 670A and 670B are movably held by guide members 675A and 675B via respective guide rails 720A and 720B.

The height of sensor 43 with respect to the floor is changed by the clockwise or counterclockwise rotation of screws 690A and 690B. The rotation force of screws 690A and 690B is transmitted from a lift driver 700 via a gear mechansim 710.

The embodiment of FIGS. 26A and 26B is suitable when many CT images of various slices in the vertical direction of object 50 are required.

FIG. 27 shows a tomographic apparatus according to another embodiment of the invention. In this embodiment, a plurality of TV cameras 730A to 730E for sensing radiation beams 39 from generator 35 are employed. TV cameras 730A to 730E are equiangularly arranged on a sensor frame 340. When each of TV cameras 730A to 730E are provided with collimator plate (37 in FIG. 1) having multi-pinholes, or provided with multi-pinhole shutter (610 in FIG. 26), the actual radiation generating point (S) of generator 35 can be calculated by CPU (51 in FIG. 2, etc.).

FIG. 28 shows a tomographic apparatus according to another embodiment of the invention, to which an electrically scanning X-ray device is adapted. Thus, in this embodiment, a ring-like target 350 for generating radiation and a ring-like radiation sensor 430 are employed. Ring target 350 and ring sensor 430 are arranged coaxially. Also, a plurality of radiation sensors 830A to 830H are coaxially and equiangularly arranged around ring sensor 430. The position of radiation generating point S is shifted, by the electrical scanning, along the ring of target 350. Then, object 50 can be subjected to radiation beams 39 from all angular direction. The position of point S may be detected by radiation sensors 830A to 830H.

The embodiment of FIGS. 1, 14, 16, 17, 24A and 24B is suitable for inspecting a horizontally wide object 50, while the embodiment of FIGS. 25, 26A, 26B and 28 is suitable for inspecting a vertically long object 50.

Figure 29:
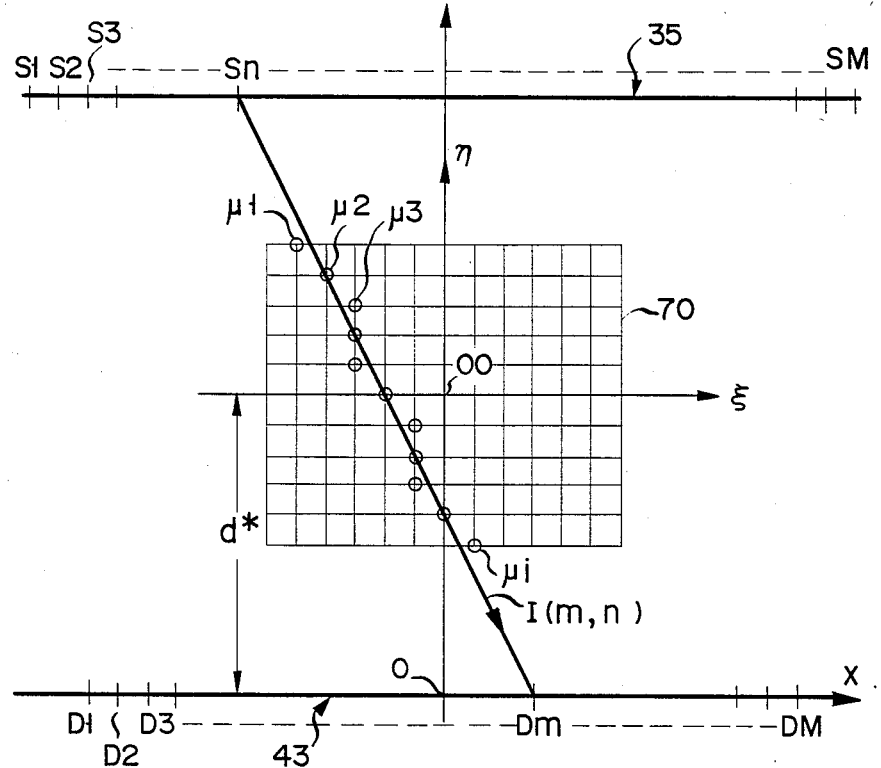
FIG. 29 shows the relationship between the radiation generating point (Sn) and the radiation sensing point (Dm), which explains how particular image data $\mu_i$ near the path of fan beam I(m,n) is sampled.

FIG. 29 shows the relationship between the radiation generating point (Sn) and the radiation sensing point (Dm). FIG. 29 explains how particular image data $\mu 1$, $\mu 2, \ldots, \mu_i$ of image reconstruction area 70, near beam path I(m,n), are sampled.

In the illustration of FIG. 29, it is assumed that beam path I(m,n) is on an x-y plane, that the sensor elements of sensor 43 are arranged along the x axis of the x-y plane, that area 70 is formed of an image reconstruction matrix defined in a $\xi$-$\eta$ plane, that the $\eta$ axis of the $\xi$-$\eta$ plane is on the y axis of the x-y plane, that the $\eta$ axis of the $\xi$-$\eta$ plane is separated, in parallel, by d* from the x axis of the x-y plane (i.e., the origin 00 of the $\xi$-$\eta$ plane is deviated by d* from the origin 0 of the x-y plane,), that beam path I(m,n) from the nth point Sn of generator 35 to the mth point Dm of sensor 43 passes through image reconstruction area 70, and that image data $\mu 1$ to $\mu_i$ of the image reconstruction matrix near beam path I(m,n) are sampled.

Under the above assumption, data of the x-y plane can be converted to data of the $\xi$-$\eta$ plane according to the following relation:

$$\left.\begin{array}{l} \xi = x \\ \eta = y - d^* \end{array}\right\} \quad (30)$$

Thus, position data Sn($\xi,\eta$) and Dm($\xi,\eta$) of points Sn and Dm with respect to the $\xi$-$\eta$ plane can be obtained, according to Eq. (30), from position data Sn(x,y) and Dm(x,0) of points Sn and Dm with respect to the x-y plane. Position data Dm(x,0) is obtained from the radiation sensing position of sensor 43. Position data Sn(x,y) can be determined from data Dm(x,0) and from the data of distances R and Lmn (FIG. 9) which are obtained in accordance with Eqs. (20) and (26).

When position data Sn($\xi,\eta$) and Dm($\xi,\eta$) of points Sn and Dm are obtained, how beam path I(m,n) passes through image reconstruction area 70 can be determined. Then, image data $\mu 1$ to $\mu_i$ near beam path I(m,n) are sampled by corresponding pixels of the image matrix in reconstruction area 70.

Figure 30:
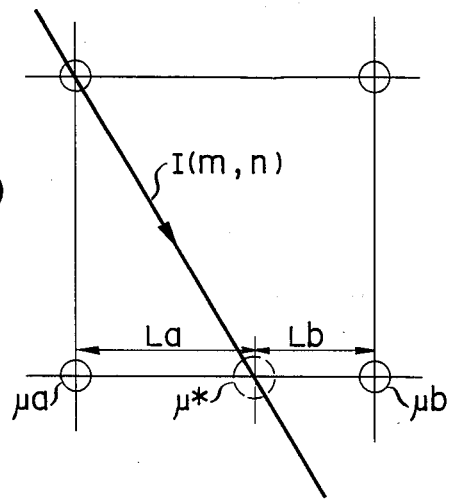
FIG. 30 explains how image data $\mu^*$ on the fan beam path is obtained from adjacent image data $\mu a$ and $\mu b$.

FIG. 30 explains how image data $\mu^*$ on the beam path is obtained from adjacent sampled image data $\mu a$ and $\mu b$. As shown in FIG. 30, if beam path I(m,n) passes between the two adjacent pixels of sampled image data $\mu a$ and $\mu b$, image data $\mu^*$ on the beam path can be obtained according to the following interpolation:

$$\mu^* = Lb \cdot \mu a + La \cdot \mu b \tag{31}$$

The CT, value of an object to be inspected, which is derived from the above sampled image data $\mu_i$ (or $\mu^*$), may be obtained from the following manner.

Figure 31:
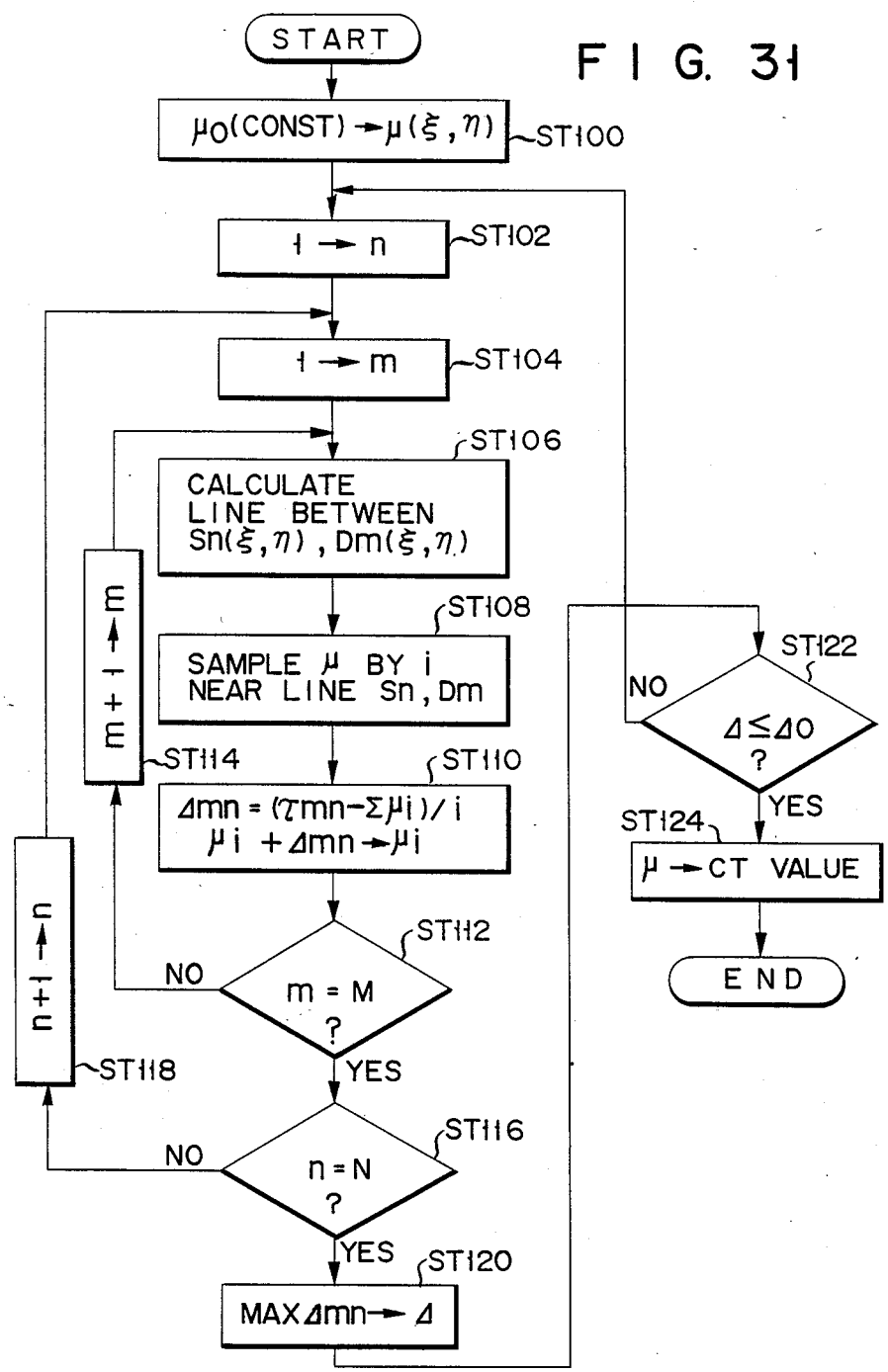
FIG. 31 is a flow chart explaining how a known sequential approximation method is applied to the present invention.

FIG. 31 is a flow chart explaining how a known sequential approximation method is utilized to obtain the CT value of an object to be inspected.

First, given data $\mu o$ (constant) is preset for initial image data $\mu(\xi,\eta)$ (step ST100). The position parameter n of radiation generating point S is set at 1 (step ST102). The position parameter m of radiation sensing point D is set at 1 (step ST104). Then, the line of beam path I(m,n) between points S1 (n=1) and D1 (m=1) is calculated according to Eq. (26) (step ST106). When the line of beam path I(m,n) is determined, particular image data $\mu 1, \mu 2, \ldots, \mu_i$ near the beam line are sampled (step ST108). According to preprocessed data $\tau m(m,n)$ with respect to the determined beam line, the sum $$\sum_i \mu_i$$

of the sampled image data $\mu_i$ and the number i of the summation, a correction amount $\Delta mn$ for correcting initial image data $\mu(\xi,\eta)$ is calculated according to the following (step ST110):

$$\Delta mn = (\tau mn - \Sigma \mu_i)/i \tag{32}$$

Then, the calculated amount $\Delta mn$ is added to data $\mu_i$ (i.e., $\mu_i + \Delta mn \rightarrow u_i$).

After calculating the correction amount $\Delta mn$, whether or not position parameter m reaches the maximum value M is checked (step ST112). If parameter m is less than M (NO at step ST112), parameter m is incremented by 1 (e.g., m is changed from 1 to 2) (step ST114), and the flow is returned to step ST 106. If parameter m is equal to the maximum value M (YES at step ST112), whether or not position parameter n reaches the maximum value N is checked (step ST116). If parameter n is less than N (NO at step ST116), parameter n is incremented by 1 (e.g., n is changed from 1 to 2) (step ST118), and the flow is returned to step ST 104.

If parameter n is equal to the maximum value N (YES at step ST116), the maximum correction amount $\Delta$ is selected from the former calculated correction amounts $\Delta mn$ (step ST120). The selected maximum correction amount $\Delta$ is compared with a predetermined reference value $\Delta o$ (step ST122). If the selected maximum amount $\Delta$ exceeds the reference value $\Delta o$ (NO at step ST122), the flow is returned to step ST 102. If the selected maximum amount $\Delta$ is equal to or less than the reference value $\Delta o$ (YES at step ST122), the image data $\mu$ being obtained at this time is used for the CT value (step ST124).

Although the operating speed achieved by the method of FIG. 31 is far lower than that achieved by the method of FIG. 5, the FIG. 31 method can be applied to a tomographic apparatus of the present invention.

While the invention has been described in connection with what is presently considered to be the most practical and preferred embodiment, it is understood that the invention is not to be limited to the disclosed embodiment but, on the contrary, is intended to cover various modifications and equivalent arrangements included within the scope of the appended claims, which scope is to be accorded the broadest interpretation so as to encompass all such modifications and equivalent structures. For instance, the embodiment of FIG. 1 may be modified such that the adjustment of the parallel relation between radiation generator system 20 and radiation sensor system 40 is effected at the system 40 side.

What is claimed is:

1. A tomographic apparatus comprising:
    radiation means having a radiation generating point for providing a radiation beam;
    sensor means having a radiation sensor for sensing the intensity of said radiation beam to provide radiation absorption data, a space being provided between said radiation means and said sensor means such that an object to be inspected by the tomographic apparatus may be inserted therein, said radiation means and said sensor means being separate units with the distance therebetween being variable;
    detector means, coupled to said radiation means and sensor means, for detecting a prescribed geometrical relationship between said radiation generating point and said radiation sensor; and
    reconstructor means, coupled to said detector means, for reconstructing CT image data from said radiation absorption data in accordance with the detected geometrical relationship between said radiation generating point and said radiation sensor;
    scan means, coupled to said radiation means, for shifting said radiation generating point so that said radiation beam scans said object;
    wherein said prescribed geometrical relationship is that a locus of points defined by shifting said radiation generating point is substantially parallel to an arrangement of radiation sensing element of said radiation sensor;
    locus detector means, coupled to said detector means, for detecting how the locus of said radiation sensing point deviates from an exact parallel relation between said locus and the arrangement of radiation sensing elements of said radiation sensor;
    locus correction means, coupled to said locus detector means, for correcting the locus of said radiation sensing point so that the deviation of said locus from said exact parallel relation is minimized.

2. A tomographic apparatus according to claim 1, wherein said sensor means includes:
    position detector means, responsive to said radiation beam, for detecting the position of said radiation generating point.

3. A tomographic apparatus according to claim 2, wherein said reconstructor means reconstructs the CT image data from said radiation absorption data in accordance with the detected position of said radiation generating point.

4. A tomographic apparatus according to claim 1, wherein said prescribed geometrical relationship is that the locus of points defined by said radiation generating point is curved around said object, and the arrangement of radiation sensing elements of said radiation sensor is curved around said object.

5. A tomographic apparatus according to claim 1, wherein said prescribed geometrical relationship is that the locus of points defined by shifting said radiation generating point, and the arrangement of radiation sensing elements of said radiation sensor, are substantially linear.

6. A tomographic apparatus according to claim 1, wherein said radiation sensor is formed of a linear sensor array.

7. A tomographic apparatus according to claim 1, wherein said radiation sensor is formed of a two-dimensional sensor array.

8. A tomographic apparatus according to claim 1, wherein said radiation means includes:
means for moving said radiation generating point along said object.

9. A tomographic apparatus according to claim 1, wherein said sensor means includes:
means for moving said radiation sensor along said object.

10. A tomographic apparatus according to claim 1, wherein said radiation means or said sensor means is moved by said locus correction means, so that said deviation is minimized.

11. A tomographic apparatus according to claim 1, wherein said detector means detects said geometrical relationship each time the radiation means and the sensor means are set around the object.

12. A tomographic apparatus according to claim 1, wherein said prescribed geometrical relationship is that the locus of shifting of said radiation generating point is substantially linear, while the arrangement of radiation sensing elements of said radiation sensor is curved around said object.

13. A tomographic apparatus according to claim 1, wherein said radiation beam defines a given image reconstruction area containing at least a part of said object, said given image reconstruction area being divided into plural regions, one region which is provided for each CT image data, and another region of which is provided for a given fixed value.

14. A tomographic apparatus comprising:
radiation means having a radiation generating point for providing a radiation beam;
sensor means having a radiation sensor for sensing the intensity of said radiation beam to provide radiation absorption data, a space being provided between said radiation means and said sensor means such that an object to be inspected by the tomographic apparatus may be inserted therein, said radiation means and said sensor means being separate units with the distance therebetween being variable;
detector means, coupled to said radiation means and sensor means, for detecting a prescribed geometrical relationship between said radiation generating point and said radiation sensor; and
reconstructor means, coupled to said detector means, for reconstructing CT image data from said radiation absorption data in accordance with the detected geometrical relationship between said radiation generating point and said radiation sensor;
scan means, coupled to said radiation means, for shifting said radiation generating point so that said radiation beam scans said object, wherein said prescribed geometrical relationship is that a locus of points defined by shifting said radiation generating point is substantially parallel to an arrangement of radiation sensing elements of said radiation sensor;
wherein said radiator means and said sensor means are associated with parallel adjust means for effecting such an adjustment that a linear line between two given points along the locus of said radiation sensing point is in parallel to a linear line between other two given points along the arrangement of radiation sensing elements of said radiation sensor.

15. A tomographic apparatus according to claim 14, wherein said parallel adjust means includes:
laser means for generating a linearly transmitted laser beam;
radiator index means, which defines said two given points along the locus of said radiation sensing point, for determining that said laser beam simultaneously passes through said two given points; and
sensor index means, which defines said other two given points along the arrangement of radiation sensing elements of said radiation sensor, for determining that said laser beam simultaneously passes through said other two given points.

16. A tomographic apparatus comprising:
radiation means having a radiation generating point for providing a radiation beam;
sensor means having a radiation sensor for sensing the intensity of said radiation beam to provide radiation absorption data, a space being provided between said radiator means and said sensor mean such that an object to be inspected by the tomographic apparatus may be inserted therein, said radiation means and said sensor means being separate units with the distance therebetween being variable;
detector means, coupled to said radiation means and sensor means, for detecting a prescribed geometrical relationship between said radiation generating point and said radiation sensor; and
reconstructor means, coupled to said detector means, for reconstructing CT image data from said radiation absorption data in accordance with the detected geometrical relationship between said radiation generating point and said radiation sensor;
wherein said reconstructor means includes:
means for calculating an estimation function $J[\mu(x,y)]$ of said CT image data with respect to an x-y plane on which said radiation beam passes, said estimation function $J[\mu(x,y)]$ being defined as:

$$J[\mu(x,y)] = \sum_m \sum_n w(m,n) \cdot |\tau m(m,n) - \tau[\mu(x,y):m,n]|^2$$

wherein n denotes the position of said radiation generating point, m denotes the position of one of radiation sensing elements contained in said radiation sensor, $w(m,n)$ denotes a given weight function, $\tau m(m,n)$ corresponds to said radiation absorption data, and $\tau[\mu(x,y):m,n]$ is represented by:

$$\tau[\mu(x,y):m,n] = \sum_x \sum_y \psi \cdot \mu(x,y)$$

wherein $\Psi$ is a given function of the intensity of said radiation beam;

means for calculating a gradient $g[\mu(x,y):x,y]$ of said estimation function $J[\mu(x,y)]$ according to the following relation:

$$g[\mu(x,y):x,y] = 2 \sum_m \sum_n w(m,n) \cdot \{\tau m(m,n) - \tau[\mu(x,y):m,n]\} \cdot \psi; \text{ and}$$

means for calculating an image correcting direction $S_i(x,y)$ according to the following relation:

$$S_i(x,y) = g[\mu(x,y):x,y] + F \cdot S_{i-1}(x,y)$$

wherein F denotes a function of $g[\mu_1(x,y):x,y]$ and $g[\mu_{i-1}(x,y):x,y]$, $g[\mu_i(x,y):x,y]$ denotes a gradient of said estimation function with respect to the ith iterated image, and $g[\mu_{i-1}(x,y):x,y]$ denotes a gradient of said estimation function with respect to the (i−1)th iterated image.

17. A tomographic apparatus according to claim 16, wherein said reconstructor means further includes:

means for calculating (i+1)th iterated CT image data $\mu_{i+1}(x,y)$ from ith iterated CT image data $\mu_i(x,y)$ according to the following relation:

$$\mu_{i+1}(x,y) = \mu_i(x,y) + \alpha_i \cdot S_i(x,y)$$

wherein $\alpha_i$ denotes a given correction amount with respect to said image correcting direction $S_i(x,y)$.

* * * * *